(12) United States Patent
Bom et al.

(10) Patent No.: US 9,616,175 B2
(45) Date of Patent: Apr. 11, 2017

(54) FROST PROTECTED INJECTION DEVICE

(75) Inventors: Lars Morten Bom, Herlev (DK); Christian Peter Enggaard, Vejby (DK); Brian Ostergaard, Graested (DK); Jacob Kollerup Jensen, Hellerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 1154 days.

(21) Appl. No.: 13/382,682

(22) PCT Filed: Jul. 8, 2010

(86) PCT No.: PCT/EP2010/059822
§ 371 (c)(1),
(2), (4) Date: Apr. 2, 2012

(87) PCT Pub. No.: WO2011/003979
PCT Pub. Date: Jan. 13, 2011

(65) Prior Publication Data
US 2012/0184917 A1    Jul. 19, 2012

Related U.S. Application Data

(60) Provisional application No. 61/224,538, filed on Jul. 10, 2009.

(30) Foreign Application Priority Data

Jul. 8, 2009   (EP) .................................. 09164871

(51) Int. Cl.
A61M 5/31      (2006.01)
A61M 5/24      (2006.01)
A61M 5/315     (2006.01)

(52) U.S. Cl.
CPC ............ *A61M 5/24* (2013.01); *A61M 5/3157* (2013.01); *A61M 5/31585* (2013.01);
(Continued)

(58) Field of Classification Search
CPC .... A61M 5/24; A61M 5/315; A61M 5/31505; A61M 5/31501; A61M 2005/31508; A61M 2005/3151; A61M 5/2425
See application file for complete search history.

(56) References Cited

U.S. PATENT DOCUMENTS 4,093,108 A *  6/1978  Hein et al. ............... 222/401
4,413,760 A   11/1983  Paton
(Continued)

FOREIGN PATENT DOCUMENTS

EP     37696 A1    10/1981
JP     0280057     3/1990
(Continued)

*Primary Examiner* — Bhisma Mehta
*Assistant Examiner* — Jenna Zhang
(74) *Attorney, Agent, or Firm* — Wesley Nicolas

(57) ABSTRACT

The invention relates to an injection device (100, 200, 300) which is capable of resisting proximal movements of a piston rod (107, 207, 307) relative to a housing (102, 202, 302), when the piston rod (107, 207, 307) is subjected to proximally directed forces below a threshold magnitude, and of allowing reversible proximal movements of the piston rod (107, 207, 307) relative to the housing (102, 202, 302), when the piston rod (107, 207, 307) is subjected to proximally directed forces of or above the threshold magnitude.

14 Claims, 13 Drawing Sheets

(52) U.S. Cl.
CPC ....... *A61M 5/31593* (2013.01); *A61M 5/2425* (2013.01); *A61M 5/315* (2013.01); *A61M 5/3146* (2013.01); *A61M 5/3156* (2013.01); *A61M 5/31505* (2013.01); *A61M 5/31551* (2013.01); *A61M 2005/2407* (2013.01); *A61M 2005/3152* (2013.01); *A61M 2005/31508* (2013.01); *A61M 2205/581* (2013.01); *A61M 2205/583* (2013.01); *A61M 2205/6081* (2013.01)

(56) References Cited

U.S. PATENT DOCUMENTS

| | | | | |
|---|---|---|---|---|
| 5,256,154 | A * | 10/1993 | Liebert | A61L 2/07 604/199 |
| 5,279,582 | A * | 1/1994 | Davison | A61J 1/2096 604/198 |
| 6,579,269 | B1 * | 6/2003 | Kleyman | A61M 5/31555 604/207 |
| 6,899,699 | B2 * | 5/2005 | Enggaard | A61M 5/20 604/207 |
| 2005/0154352 | A1 * | 7/2005 | Gurtner | A61M 5/31553 604/208 |
| 2006/0235086 | A1 | 10/2006 | Maskaly et al. | |
| 2007/0185440 | A1 * | 8/2007 | Matsumto | A61M 5/2448 604/85 |
| 2008/0140018 | A1 * | 6/2008 | Enggaard | A61M 5/20 604/207 |
| 2010/0186739 | A1 * | 7/2010 | Kronestedt | A61M 5/20 128/203.12 |
| 2010/0200787 | A1 * | 8/2010 | Hirschel | A61M 5/31501 251/89 |

FOREIGN PATENT DOCUMENTS

| | | |
|---|---|---|
| JP | H08-504352 A | 5/1996 |
| JP | 2002-515268 A | 5/2002 |
| JP | 2003180832 A | 7/2003 |
| JP | 2004535900 A | 12/2004 |
| JP | 2005270579 A | 10/2005 |
| JP | 200768630 | 3/2007 |
| JP | 2008541907 A | 11/2008 |
| JP | 05305140 B2 | 10/2013 |
| WO | 0041752 A1 | 7/2000 |
| WO | 03011371 A2 | 2/2003 |
| WO | 2004006997 A1 | 1/2004 |
| WO | 2009/057378 A1 | 5/2009 |

* cited by examiner

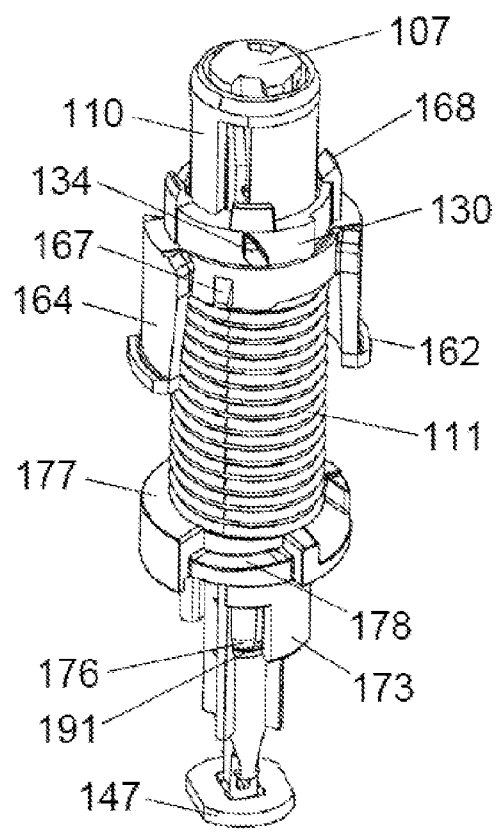
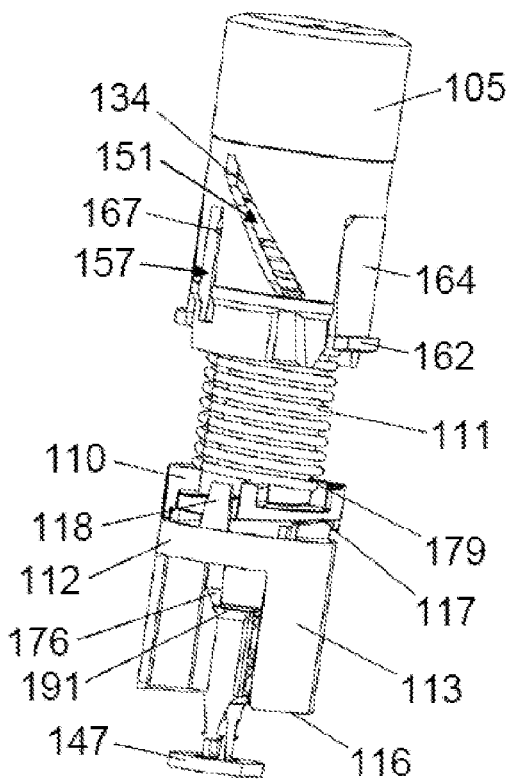
Fig. 14  Fig. 15
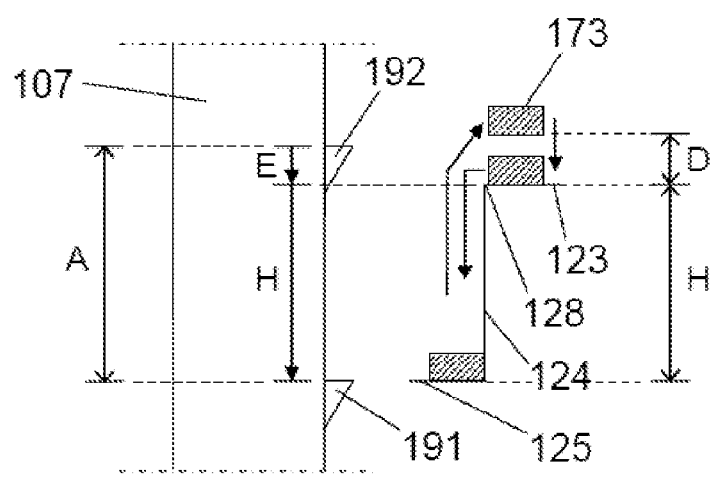
Fig. 16

FROST PROTECTED INJECTION DEVICE

CROSS-REFERENCE TO RELATED APPLICATIONS

This application is a 35 U.S.C. §371 national stage application of International Patent Application PCT/EP2010/059822 (published as WO 2011/003979), filed Jul. 8, 2010, which claimed priority of European Patent Application 09164871.7, filed Jul. 8, 2009; this application further claims priority under 35 U.S.C. §119 of U.S. Provisional Application 61/224,538, filed Jul. 10, 2009.

FIELD OF THE INVENTION

The present invention relates to an injection device for administering a liquid drug.

BACKGROUND OF THE INVENTION

Injection devices, such as injection pens, are widely used for self administration of liquid drugs by people in need of therapeutic treatment. Many injection devices are capable of repeatedly setting and injecting either a fixed or a variable volume of drug upon operation of respective dose setting and injection mechanisms in the device. Some injection devices are adapted to be loaded with a prefilled drug reservoir containing a volume of drug which is sufficient to provide for a number of injectable doses. When the reservoir is empty, the user replaces it with a new one and the injection device can thus be used again and again. Other injection devices are prefilled when delivered to the user and can only be used until the drug reservoir has been emptied. The various injection devices typically expel the drug by advancing a piston in the reservoir using a motion controlled piston rod.

In order for an injection device to deliver accurate doses it is required that the piston rod is in contact with the piston in the reservoir at any time during the action of the piston rod drive following an activation of the injection mechanism. During transportation and handling of the injection device there is, however, a risk of introducing an undesired slack between the piston rod and the piston which should then be eliminated before an injection, e.g. by carrying out a priming operation. Certain injection devices are provided with a unidirectional coupling mechanism preventing the piston rod from moving proximally, or backwards, in the injection device. As an example, WO 2004/006997 discloses an administering apparatus incorporating a piston rod with two rows of serrated teeth for successive engagement with blocking tongues in a holding part preventing a returning movement of the piston rod in any axial position. Such a non-return arrangement practically eliminates the possibility of slack between the piston rod and the piston once the two components have initially been brought together.

If an injection device accommodating a liquid drug is for any reason exposed to temperatures below the liquid drug's freezing point, the liquid will expand in the reservoir causing a relatively large pressure on the reservoir walls, including the piston. When there is no slack between the piston rod and the piston, the piston rod drive will consequently be exposed to a relatively large backward directed force from the piston via the piston rod. Especially for injection devices employing a unidirectional ratchet and pawl drive mechanism the coupling between the piston rod and the piston rod drive may not be able to withstand such a large force, potentially leading to breakage of vital components in the device, thereby either introducing a risk of malfunction or rendering the device useless.

Some liquid drugs should be stored within certain temperature limits to maintain their desired therapeutic effect. For example, to avoid bacteria growth some liquid drugs should be stored refrigerated. However, accidentally placing the drug container too close to a highly active cooling element may cause the drug to freeze. This issue is particularly relevant for people living in a hot climate. In case the liquid drug itself is not spoiled by the freezing it would be convenient if the encapsulating delivery device was not spoiled either, so the user would avoid wasting the drug anyway. Therefore, it is desirable to provide an injection device which is capable of resisting temperatures below the freezing point of the contained drug, i.e. which is not damaged and rendered useless as a result of the drug expanding in the reservoir.

SUMMARY OF THE INVENTION

Having regard to the above it is an object of the invention to provide an injection device which is able to administer one or more doses of a liquid drug, the one or more doses being administered reliably/consistently and with high accuracy.

It is a further object of the invention to provide an injection device allowing for a temporary expansion of the drug containing reservoir which does not damage the injection mechanism and which does not affect the dose accuracy of the device.

In the disclosure of the present invention, aspects and embodiments will be described which will address one or more of the above objects or which will address objects apparent from the below disclosure as well as from the description of exemplary embodiments.

In an aspect of the invention an injection device for administering a liquid drug is provided, the injection device comprising: a variable volume reservoir adapted to contain the liquid drug and comprising an outlet and a movable wall, and injection means comprising an actuation member adapted to cause a displacement of the movable wall in a first direction, the injection device being configured to allow a reversible movement of the actuation member in a second direction in response to a force (e.g. a single force, a resulting force, a distribution of forces) acting on the actuation member in the second direction.

In a specific embodiment of the invention the second direction is opposite to, or at least substantially opposite to, the first direction.

If the drug expands in the reservoir, e.g. due to a temperature decrease leading to a phase change, the forces act on the actuation member via the movable wall, and the configuration of the injection device therefore allows a displacement of the movable wall in the second direction without causing damage to the injection means.

The injection means, or at least a constituent thereof, may be configured to deform or displace in the second direction in response to forces acting in the second direction and to elastically recover to the original state in response to a discontinuation of the forces acting in the second direction.

The injection device may further comprise bias means for biasing the actuation member in the first direction. This may provide for an automatic return of the actuation member to its original position upon a discontinuation of a displacing force acting in the second direction.

In an exemplary embodiment, the bias means forms part of the injection means, whereby an injection device is provided which is capable of both automatically injecting a dose of the liquid drug and automatically returning the actuation member to its original position upon a discontinuation of a force acting in the second direction, without requiring extra construction parts.

The injection means may be an injection mechanism and may further comprise an actuation member drive arrangement, e.g. adapted to transmit a biasing force from the bias means to the actuation member. The drive arrangement may consist of a single, movable drive element or it may comprise a plurality of interacting elements, e.g. a movable drive element and a stationary element. Specifically, the drive arrangement may be of the type which is able to undergo relative motion with respect to the actuation member in one direction and to engage and slave the actuation member in another direction.

In one embodiment of the invention the injection mechanism is configured to allow a displacement of the actuation member and/or the drive arrangement in the second direction against the bias of the bias means in response to a force acting in the second direction and to return the actuation member and/or the drive arrangement to substantially the initial position upon discontinuation of the force acting in the second direction. Particularly, the actuation member comprises a contact surface adapted to abut or engage with the movable wall when the movable wall is displaced during an injection, and the injection mechanism is configured to allow a displacement of the contact surface from a first position to a second position, relative to the outlet, in response to a force acting in the second direction and to return the contact surface to substantially the first position upon discontinuation of the force acting in the second direction.

The bias means may comprise elastically deformable geometrical configurations in or of the injection device, energy means, such as a spring member, or indeed any means suitable for biasing the force transferring means and/or the actuation member in a certain direction, e.g. towards the reservoir outlet.

The reservoir may be a rigid container having a movable wall, such as a cartridge comprising an axially displaceable piston. Alternatively, the reservoir may be a flexible container, such as a compressible bag, or a partly rigid and partly flexible container.

The injection device may further comprise a removable cap, and a cap receiving portion adapted to be in abutment or engagement with the cap when the cap is mounted on the injection device. The cap may comprise an interface for coupling with the injection mechanism via the cap receiving portion. The interface may be a contact point or surface adapted to abut or engage with the drive arrangement or an intermediate part being coupled with the drive arrangement.

The removable cap may be adapted to cover an outlet portion of the injection device, such as a needle holding portion or a jet injection nozzle, when the injection device is not in use. Thereby the removable cap is capable of e.g. protecting a needle mounted on the needle holding portion, preventing needle sticks and preventing accidental spilling of the liquid drug. The cap can be removed when it is desired to inject a dose, thereby uncovering the needle holding portion.

The cap receiving portion may be a portion of the injection device which is adapted to receive and hold the removable cap when the cap is mounted on the injection device.

The cap receiving portion may comprise means for retaining the cap, such as a bayonet joint, a threaded portion, a snap lock, etc. The cap receiving portion may be adapted to receive the cap when the cap is mounted on the injection device to cover the distal, or outlet, portion of the injection device. Alternatively, the cap receiving portion may be adapted to receive the cap when the cap is mounted on the proximal portion of the injection device.

The injection device may further comprise a housing, e.g. of cylindrical form defining a general longitudinal axis, of a box like form, or of another relevant form. In a specific embodiment of the invention a dismounting of the cap from the cap receiving portion causes the actuation member and/or the drive arrangement to undergo an axial displacement.

In another aspect of the invention a mechanical injection device for administering a liquid drug is provided, the injection device comprising: a variable volume reservoir adapted to contain the liquid drug and comprising an outlet and a movable wall, and an injection mechanism comprising an actuation member adapted to cause a displacement of the movable wall in a first direction, and bias means for biasing the actuation member in the first direction, the injection mechanism being configured to allow a reversible movement of the movable wall in a second direction in response to forces acting on the movable wall in the second direction.

In one embodiment of the invention the injection mechanism is configured to allow a movement of the movable wall in the second direction from a first position to a second position in response to the application of a force in the second direction on the movable wall and to move the movable wall in the first direction, utilising energy stored in the bias means, from the second position to substantially the first position upon a discontinuation of the force. Thereby, it is ensured that the movable wall and the injection mechanism are returned to their respective initial states automatically, i.e. without the user having to manipulate any parts of the injection device, when the load terminates.

The actuation member may be subjected to forces in the second direction under normal use circumstances of the injection device, e.g. during transport or during dose setting where another construction part touches or interacts with the actuation member. To ensure dose accuracy it is, however, important that the actuation member is not able to undergo uncontrolled movements relative to the movable wall, because this will make a synchronous movement of the two during a subsequent injection impossible.

Thus, in a further aspect of the invention, a mechanical injection device for administering a liquid drug is provided, the injection device comprising: a variable volume reservoir adapted to contain the liquid drug and comprising an outlet and a movable wall, an injection mechanism comprising an actuation member adapted to cause a displacement of the movable wall in a first direction, a drive arrangement adapted to cause movement of the actuation member, and optionally bias means for causing a bias on the actuation member in the first direction, and a coupling mechanism, e.g. comprising an engagement structure, for affecting movements of the actuation member, at least in a second direction. The engagement structure is suitable for respective coupling with and decoupling from the injection mechanism, e.g. the actuation member and/or one or more parts of the drive arrangement, and the injection device is configured to couple the engagement structure and the injection mechanism, e.g. the actuation member, to prevent a movement of the actuation member in a second direction in response to a force acting on the actuation member, when this force has a magnitude which is smaller than a threshold value, and to reversibly decouple the engagement structure and the injection mechanism to allow a reversible movement of the actuation member in the second direction in response to a force acting on the actuation member, when this force has a magnitude which is equal to or greater than the threshold value.

Such an arrangement provides for completely synchronised movements of the movable wall and the actuation member, both in the first direction and in the second direction. Thereby, it is ensured that dose accuracy is maintained throughout the lifetime of the injection device, no matter if the actuation member is subjected to a relatively small force in connection with e.g. the setting of a dose (in which case it will not move in the second direction away from the movable wall) or subjected to a relatively large force due to the drug expanding in the reservoir (in which case it will move in the second direction together with the movable wall and return together with the movable wall when the drug resumes its original density).

The reversible decoupling of the engagement structure and the actuation member comprises non-destructively decoupling the engagement structure and the actuation member, thereby ensuring that the engagement structure and the actuation member are capable of a subsequent operative mutual coupling.

In some embodiments, the drive arrangement is adapted to interact with the actuation member and force the actuation member in the first direction under the influence of the bias means. This interaction may e.g. involve a unidirectional ratchet mechanism, in which case the drive arrangement is adapted to engage with the actuation member and slave it in the first direction, or a screw thread coupling between the actuation member and the drive arrangement, in which case e.g. a rotation of a drive member causes a translational movement of the actuation member in the first direction.

The injection device may further comprise a housing, and the engagement structure may provide a coupling between the housing and the actuation member for preventing movements of the actuation member in the second direction relative to the housing, the coupling being configured to reversibly decouple the housing and the actuation member in response to a force acting on the actuation member in the second direction of a magnitude which is equal to or greater than the threshold value.

In one embodiment of the invention the actuation member comprises teeth and the engagement structure is a deflectable pawl adapted to engage a tooth and prevent movements of the actuation member in the second direction when the actuation member is subjected to a force in the second direction which is below the threshold value and to reversibly disengage with the tooth when the actuation member is subjected to a force in the second direction which is of or above the threshold value.

In another embodiment, the actuation member comprises a screw thread which is in engagement with a mating thread on a stationary part of the drive arrangement and further rotationally locked with respect to a movable part of the drive arrangement in such a manner that e.g. clockwise rotation of the movable part of the drive arrangement leads to clockwise rotation of the actuation member as well as to translational advance through the stationary part of the drive arrangement. Circumferentially arranged teeth on the inner housing wall are adapted to engage with a deflectable pawl on the movable part of the drive arrangement in such a manner that relative rotational movement between the housing and the movable part of the drive arrangement is allowed in one direction and prevented in the opposite direction as long as the contact force is below a certain size, corresponding to when the actuation member is subjected to a force in the second direction which is below the threshold value. When the actuation member is subjected to a force in the second direction which is of or above the threshold value the deflectable pawl and the tooth which it contacts are adapted to reversibly disengage to thereby allow rotation in said opposite direction, whereby the actuation member is allowed to reversibly translate in the second direction through the threaded engagement with the stationary part of the drive arrangement.

In yet another embodiment, the actuation member is a threaded rod being in engagement with a nut member in the injection device. The engagement is such that a (for example) clockwise rotation of the rod is converted to a translational movement by the interaction with the nut member. The nut member comprises flexible jaws which hold a self-locking screw thread section. This means that if the rod is subjected to an axial, or translational, force in the second direction it cannot move in the second direction by rotating counter-clockwise back through the tread. However, if the rod is subjected to a force in the second direction which is of or above the threshold value the flexible jaws will deflect away from the rod, whereby the threaded section disengages from the rod and the rod is free to move, non-rotationally, in the second direction. When the force is terminated the flexible jaws will return to their original position and the rod will once again be in threaded engagement with the nut member.

The injection device may be of the kind which is able to deliver only a single dose of the drug. Alternatively, the injection device may be of the kind which is able to repeatedly set and deliver a dose of the drug. In that case, the injection device further comprises dose setting means operable to set a dose. In a specific embodiment, the injection device is able to repeatedly set and deliver a predetermined dose.

The dose setting means is the part of the injection device which is operated when a dose is being set. The dose setting means comprises a mechanism which brings elements of the injection device into such relative positions that a given amount of drug will be delivered upon operation of the injection mechanism. The injection mechanism is the part of the injection device which, when operated, is causing a set dose to be injected. The injection mechanism comprises a force transferring element, e.g. a movable actuation member, being adapted to cooperate with the movable wall, e.g. a piston, of the reservoir in such a manner that operation of the injection mechanism causes the actuation member to move whereby the piston is moved inside the reservoir in a direction which causes liquid drug to be expelled from the reservoir, e.g. via a needle in a needle assembly attached thereto. The dose setting mechanism and the injection mechanism may share one or more structural and/or functional elements.

The bias means may comprise energy means acting to release stored energy during injection of a dose of drug, the released energy causing the dose to be injected. The energy means may be connected to the dose setting means in such a manner that energy is stored in the energy means during setting of a dose.

The energy means may comprise a spring member which may be adapted to be loaded along its centre axis, e.g. by compressing the spring or elongating the spring. Alternatively, or additionally the spring may be adapted to be loaded about its centre axis, e.g. by mutually twisting the respective spring end portions.

The actuation member drive arrangement may comprise a drive member being coupled with the energy means in such a manner that movement of the drive member causes the energy means to store and/or release energy and/or, conversely, in such a manner that release of energy from the energy means causes the drive member to move. The energy means may in that respect comprise a compression spring which is rotationally pre-stressed to bias the drive member in both a specific translational direction and a specific rotational direction. The drive member may therefore also serve as a spring compressing element. Alternatively, the energy means may comprise other arrangements capable of storing and releasing energy for translational and rotational motion, such as for example two or more springs, each being able to provide a share of the energy needed for translational and rotational motion, e.g. a compression spring capable of providing energy for translational motion and a torsion spring capable of providing energy for rotational motion, an axially compressible torsion rod or an arrangement comprising a rotationally pre-stressed tension spring.

The actuation member may comprise a set of axially spaced apart teeth for engagement with one or more engagement elements, and the drive member may comprise an engagement element adapted to engage with the actuation member teeth. In such an embodiment, when the dose setting means is operated to set a dose the drive member will undergo relative motion with respect to the actuation member whereby the engagement element will be moved out of engagement with a tooth on the actuation member and moved along the actuation member to pass a more proximally positioned tooth. When the injection mechanism is subsequently operated to inject the set dose the engagement element will engage the tooth it just passed and the drive member will move distally in the housing while slaving the actuation member.

In an embodiment of the invention the injection mechanism is configured to allow the drive member to move a distance in the second direction in response to the actuation member being subjected to a force in the second direction which is equal to or greater than the threshold value and to return the drive member to its original position upon a discontinuation of the force on the actuation member. Once the threshold value is reached the actuation member will move into engagement with the drive member and bias the drive member in the second direction against the biasing force of the spring member. The drive member will then compress the spring member further, whereby the spring member stores extra energy for translational motion, until an equilibrium condition occurs. When the force on the actuation member ceases the spring member will release the stored extra energy and move the drive member in the first direction back to the position in which it was originally engaged by the actuation member. During this return displacement the drive member slaves the actuation member which in turn slaves the movable wall.

Guide means may be provided for guiding the movement of the drive member and/or the actuation member. The guide means may form part of the housing or may comprise a separate element having a fixed position relative to the housing. Alternatively, or additionally, the guide means may comprise an element capable of moving relative to the housing.

The guide means may be configured to enable the drive member and the actuation member to perform a purely translational relative motion during one part of the relative motion and to perform a combined translational and rotational relative motion during another part of the relative motion. The guide means may comprise a first resting surface, or first retention plateau, for supporting the drive member in a well-defined axial position, and a second resting surface, or second retention plateau, for supporting the drive member in another well-defined axial position. In one particular embodiment the axial distance between the first retention plateau and the second retention plateau corresponds to the axial displacement of the drive member during an injection.

Alternatively, the guide means may be configured to define a maximum extent of rotational movement of the drive member, e.g. during an injection. In that case, the guide means may comprise a rotational stop for the drive member, or for another part being rotationally interlocked with the drive member.

In a specific embodiment of the invention the cap comprises a round-going edge capable of transferring a force to the drive member, or to an intermediate element being coupled with the drive member, such that when the cap is mounted on the injection device at the cap receiving portion the drive member is forced to take up a certain position with respect to the cap receiving portion in which the drive member is out of engagement with the actuation member. As long as the cap is mounted on the injection device the drive member is held in this position against the biasing force of the bias means.

A dismounting of the cap from the cap receiving portion may cause the drive member to undergo a displacement whereby it is forced to engage with the actuation member and move the actuation member into abutment with the movable wall to exert a biasing force on the movable wall. Alternatively, or additionally, a dismounting of the cap from the cap receiving portion may cause the actuation member to displace the movable wall.

In an even further aspect of the invention, a drug delivery device is provided comprising: a reservoir comprising an outlet and a movable wall, an actuation member adapted to cause a movement of the movable wall in a first direction, a pliable engagement structure, and a body surface having a number of structural irregularities for successive engagement with the pliable engagement structure, wherein at least one structural irregularity comprises a contact surface which is angled obtusely relative to the body surface to provide for a locking engagement between the pliable engagement structure and the body surface when the pliable engagement structure is subjected to a force in a second direction substantially opposite to the first direction, the force being of a magnitude which is smaller than a threshold value, and to provide for a non-destructive disengagement of the pliable engagement structure and the body surface when the pliable engagement structure is subjected to a force in the second direction, the force being of a magnitude which is equal to or greater than the threshold value.

The structural irregularities may be indentations in and/or protrusions on the body surface.

The body surface may be a surface of the actuation member. Alternatively, the body surface may be a surface of another part of the drug delivery device.

The system that makes up an injection device usually comprises two parts, an energizer comprising an injection mechanism, and optionally a dose setting mechanism, which energizer is contained in a first body part of the injection device, and a reservoir which is embedded in a second body part of the injection device, often referred to as the reservoir holder.

In an even further aspect of the invention, a system is provided, comprising: an energizing portion comprising an injection mechanism with an actuation member and bias means, and a variable volume reservoir containing a liquid drug and comprising a movable wall, the actuation member and the movable wall being capable of mutual displacement in a first direction, and the energizing portion being configured to allow a reversible mutual displacement of the actuation member and the movable wall in a second direction in response to a force acting on the movable wall in the second direction.

The second direction may be opposite to the first direction. Further, the force may be acting on the movable wall.

The energizing portion may further comprise an engagement structure for respective engagement with and disengagement from the actuation member, the engagement structure being adapted to engage with the actuation member to prevent mutual displacement of the actuation member and the movable wall in the second direction when the actuation member is subjected to a force of a magnitude which is smaller than a threshold value and to reversibly disengage from the actuation member to allow a reversible mutual displacement of the actuation member and the movable wall in the second direction when the actuation member is subjected to a force of a magnitude which is equal to or greater than the threshold value.

The reservoir and the energizing portion may be inseparably coupled in which case the injection device does not allow the reservoir to be replaced by another reservoir. This means that once the original reservoir has been emptied, or rather once the last complete dose has been injected, the entire device cannot be re-used and must be discarded. Any successful attempt to separate the reservoir from the energizing portion will render the injection device useless due to disruption of the reservoir holder or the connection between the reservoir holder and the energizing portion.

In relation to the above aspects and embodiments of the invention it is noted that the respective allowed reversible movements of the actuation member and/or the movable wall in the second direction are non-destructive. In the present context, this should be interpreted to mean that no parts or members of the injection device essential to the general functionality, e.g. the carrying out of an injection or a dose setting, of the injection device are broken or otherwise destroyed as a consequence of said movements. In other words, in case the injection device is of the type which is able to deliver multiple doses of drug the device is capable of performing a number of dose setting and injection cycles, corresponding to the remaining amount of drug in the reservoir, following the return movement of the element or elements in question. In case the injection device is of the single shot type the device is capable of performing a single dose injection of the drug following the return movement of the element or elements in question.

The threshold value may be preset by the manufacturer, e.g. by choosing the frictional relationships between the mutually contacting elements and the configurations of the interfacing surfaces such that the threshold is reached when a certain force is acting on the actuation member in the second direction. In that respect, the threshold value may in principle be set arbitrarily.

The frictional relationships between the mutually contacting elements may be established via the choice of materials for the interacting components. In one embodiment the interacting components are made of plastic.

The configurations of the interfacing surfaces may comprise respective angles of the teeth and/or the specific design of the engagement structure. In that respect, one or more teeth may be angled obtusely relative to the body surface of the toothed member. This will provide for a firm engagement between the engagement structure and the toothed member so long as the contact forces in the interface region are relatively small, e.g. so long as the actuation member causes a force of about 2-5 N on the engagement structure. However, for greater contact forces the angled teeth allow for a sliding disengagement of the engagement structure and the toothed member. If the engagement structure is somewhat pliable it will deflect during the disengagement and elastically recover after having passed the respective tooth.

In one embodiment of the invention the threshold value equals the biasing axial force or torque of the spring member. Thereby, when the engagement structure disengages from a tooth and the actuation member moves in the second direction, the spring member will be compressed or twisted beyond its initial compressed or twisted state.

It is noted, however, that the threshold value does not need to be known by the manufacturer as such. The threshold value may be a threshold "interval" in the sense that the manufacturer may choose to configure the injection device such that the threshold value is guaranteed to be greater than a certain minimum value sufficient to obtain the desired features of the injection device, e.g. such that the engagement structure is able to prevent movements of the actuation member in the second direction at least during dose setting. This way the injection device will function as described in the present text without the manufacturer knowing the exact magnitude of the force that will cause the engagement structure to move out of engagement with the actuation member and thereby allow a displacement of the actuation member in the second direction. The minimum value sufficient to obtain the desired features of the injection device may be determined by experimentation and may optionally be chosen to incorporate a safety margin.

Arrangements as the above described have the effect that should the drug deliberately or inadvertently be exposed to temperatures that causes it to freeze it is free to expand in the reservoir because the construction of the injection device, e.g. the configuration of the injection mechanism, allows the movable wall to move in another direction than the one intended for injection of the drug without resulting in damages to the device. Further, since the volume of drug delivered in the course of an injection depends only on a firm engagement between the actuation member and the drive member and on the distance between the first retention plateau and the second retention plateau, the arrangements guarantee that the dose injected following a drug freeze and thawing out is the same as it would be otherwise. This is because following the thawing out of the drug the actuation member and the drive member will be positioned relative to the guide member such that when a user operates the injection device the components will undergo the same movements as they would under normal circumstances. Specifically, the drive member and the actuation member will be in firm engagement when the drive member is positioned on the first retention plateau. In other words a freezing of the drug will not affect the dose accuracy of the injection device.

In the present context the term 'mechanical injection device' should be interpreted to mean an injection device which is mechanically operated as opposed to electromotor driven injection devices.

In the present context the term 'actuation member' is used to designate the mechanical element that transfers a driving force to the movable wall of the reservoir. The 'actuation member' may comprise a rod and a rod foot, the rod foot being the element physically contacting the movable wall. The rod and the rod foot can be made as two separate pieces or they can be made as one integral element. Alternatively, the 'actuation member' comprises a rod without any foot in which case the rod itself is adapted to physically contact the movable wall. In case the reservoir is a cartridge type reservoir comprising an axially displaceable piston the 'actuation member' may be a piston rod with or without a piston rod foot. It is noted that the term 'actuation member' also encompasses other suitable structures for transferring a driving force to the movable wall, such as e.g. a plate or a diaphragm.

In the present context the term 'liquid drug' should be interpreted to mean a drug in a liquid state, such as, e.g., a solution or a suspension.

In the present context the term 'predetermined dose' should be interpreted in such a manner that when the dose setting means is operated a specific fixed dose is set, i.e. it is not possible to set an arbitrary dose. However, the predetermined dose may be variable in the sense that it may be possible to initially set the injection device to a selected dose, and the dose setting means will then set this selected dose each time the dose setting means is operated. It should be noted that the term 'predetermined dose' does not rule out that the injection device may have a priming function.

In the present specification reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in at least that one aspect or embodiment of the invention, but not necessarily in all aspects or embodiments of the invention. It is emphasized, however, that any combination of features, structures and/or characteristics described in relation to the various aspects and embodiments of the invention is encompassed by the invention unless otherwise indicated herein or clearly contradicted by context.

The use of any and all examples, or exemplary language (e.g., such as, etc.), in the text is intended merely to illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 14 is a perspective view of parts of an injection mechanism, showing a relation between the drive member, the piston rod, the spring, the spring holding element and the coupling element, FIG. 15 is a perspective view of the injection mechanism of FIG. 14, including the injection button and the push element, FIG. 16 is a two-dimensional representation of the movement of the drive member during dose setting, respectively injection.

In the figures like structures are mainly identified by like reference numerals.

DESCRIPTION OF EXEMPLARY
EMBODIMENTS

When in the following relative expressions, such as "clockwise" and "counter-clockwise" and "proximally" and "distally", are used, these refer to the appended figures and not necessarily to an actual situation of use. The shown figures are schematic representations for which reason the configuration of the different structures as well as their relative dimensions are intended to serve illustrative purposes only.

Figure 1:
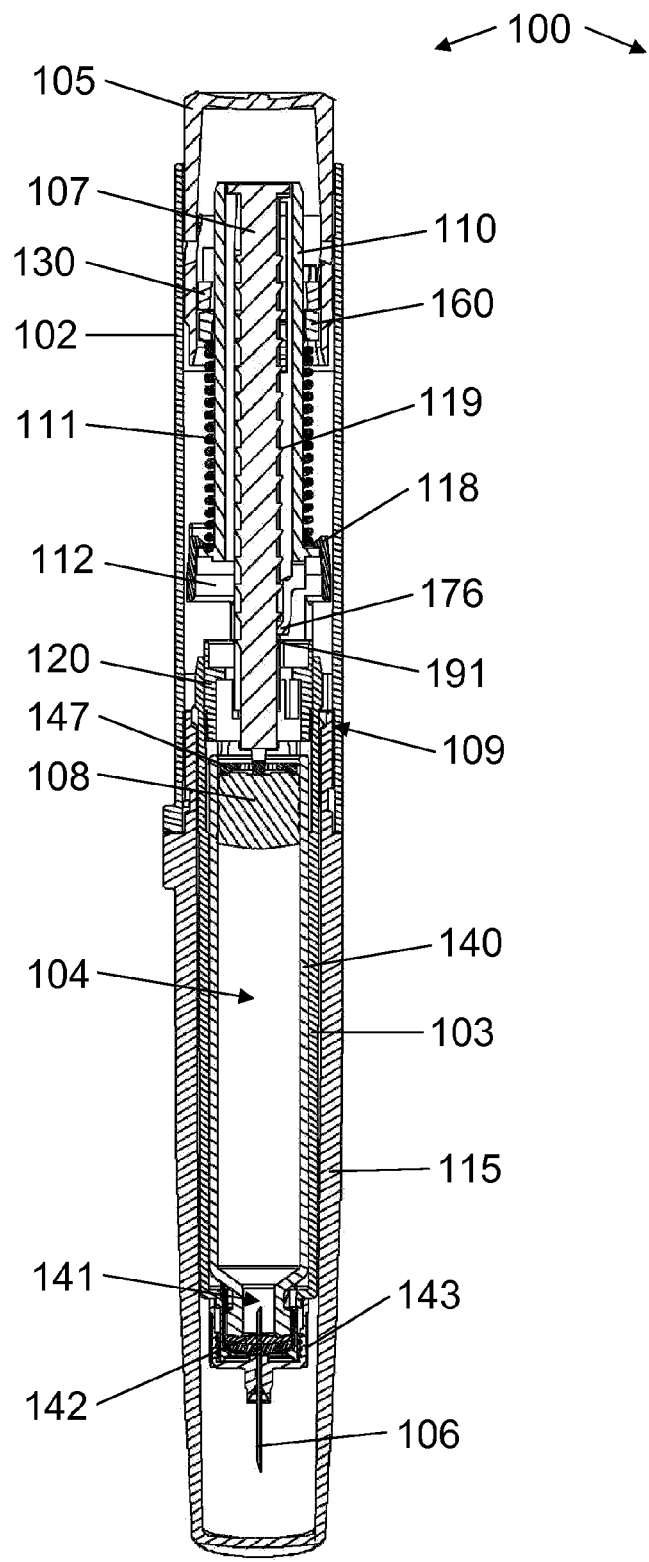
FIG. 1 is a cross sectional view of an injection device according to an embodiment of the invention before the first injection.

FIG. 1 shows an injection device 100 according to an exemplary embodiment of the invention. The injection device 100 is in a loaded state as delivered from the manufacturer, i.e. it has not yet been used for injection. The injection device 100 comprises a housing 102 and a cartridge holding part 103 for supporting a cartridge 104 which contains the liquid drug. The liquid drug is positioned between a piston 108, which is capable of moving axially in the cartridge 104, a tubular cartridge wall 140, and a self-sealing septum 142 covering a drug outlet 141. The liquid drug is intended to flow through an injection needle 106 attached to the injection device 100 via a needle hub interface 143 when the piston 108 is advanced in the cartridge 104. A cap 115 is mounted at a cap receiving portion 109 in the housing 102, whereby it protects the cartridge 104 and covers the drug outlet 141. An injection button 105 being capable of reciprocating axial motion with respect to the housing 102 is shown in a position where it protrudes from the distal end of the housing 102.

A piston rod 107 is attached to the piston 108 via a piston rod foot 147 and operatively coupled to the injection button 105 such that when the cap 115 is off and the injection button 105 is pressed against the housing 102 the piston rod 107 will advance axially through the housing 102 a certain distance, thereby displacing the piston 108 in the cartridge 104 an equivalent distance to inject a desired amount of drug through the outlet 141.

The movement of the piston rod 107 is realised through a coupling ring 130 being in engagement with a helical track (not visible) in the injection button 105, and a driver 110 which is in engagement with the coupling ring 130 and which is adapted to engage with, and transmit a driving force to, the piston rod 107. The driver 110 is powered by a spring 111 which is a torsionally pre-tensioned compression spring capable of storing and releasing energy for both translational and rotational motion. One end of the spring 111 is retained in a spring base 160, which is both translationally and rotationally fixed relative to the housing 102, and the other end of the spring 111 is in engagement with the driver 110 in such a way that the spring 111 and the driver 110 are able to interchange both forces and torques. The driver 110 is thus capable of performing both translational and rotational motion relative to the housing 102. The spring 111 may for example be torsionally pre-tensioned during assembly of the injection device 100, e.g. by mutually twisting its two end parts a half or a full turn. During dose setting and injection, the movement of the driver 110 is guided by a guide member 120 and a push element 112, which is in engagement with the driver 110 via a couple of snap arms 118. The driver 110 comprises a deflectable pawl 176 which is adapted to engage with a tooth 119 on the piston rod 107 when the driver 110 moves in the distal direction and to ride over a tooth 119 when the driver 110 moves in the proximal direction. In FIG. 1 the pawl 176 is spaced apart from a distal most tooth 191, i.e. the driver 110 is out of engagement with the piston rod 107.

Figure 2:
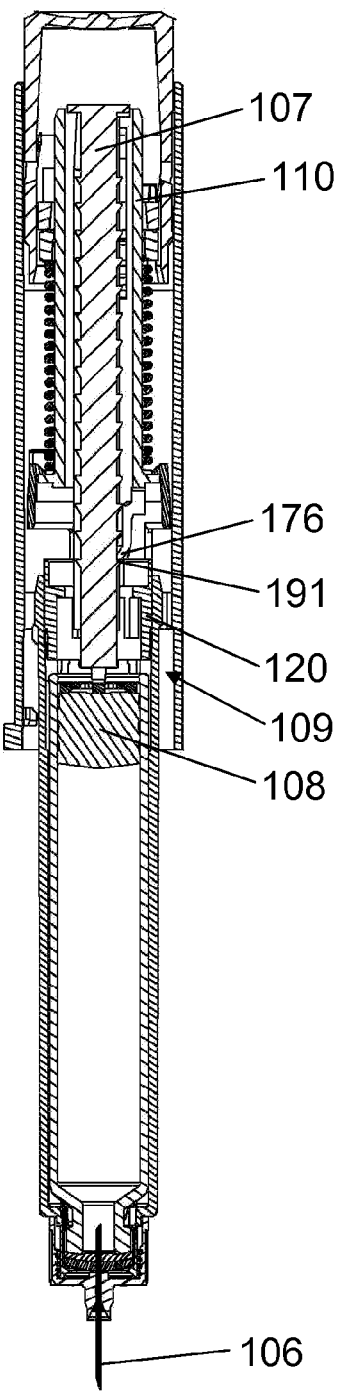
FIG. 2 is a cross sectional view of the injection device of FIG. 1 where the cap has been dismounted and the device is primed.

In FIG. 2 the cap 115 has been removed from the cap receiving portion 109. This has lead to an automatic priming of the injection device 100 by which the pawl 176 is firstly forced distally by the spring 111 into engagement with the distal most tooth 191 and the piston rod 107 is subsequently slaved by the driver 110 to displace the piston 108 a small distance (not visible) in the cartridge 104. The automatic priming sequence will be explained in more detail below.

Figure 3:
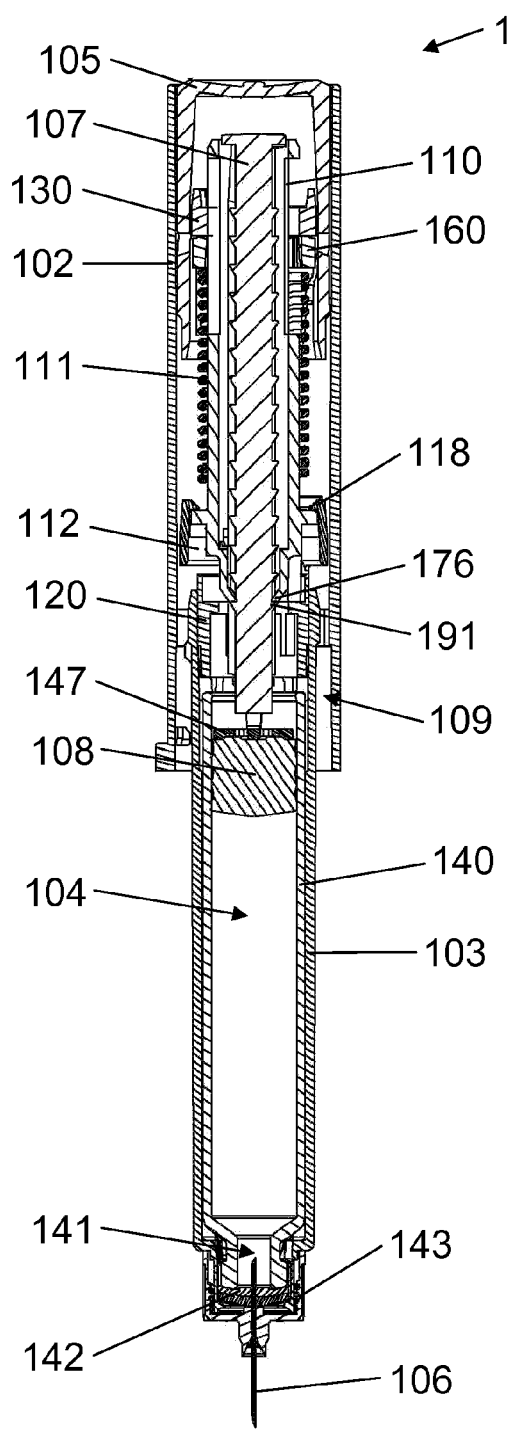
FIG. 3 is a cross sectional view of the injection device of FIG. 1 after the first injection.

FIG. 3 shows the injection device 100 following the first injection. The injection button 105 has been pressed against the housing 102 which has resulted in an activation of the spring 111 and a movement of the piston 108 corresponding to the set dose.

Figure 4:
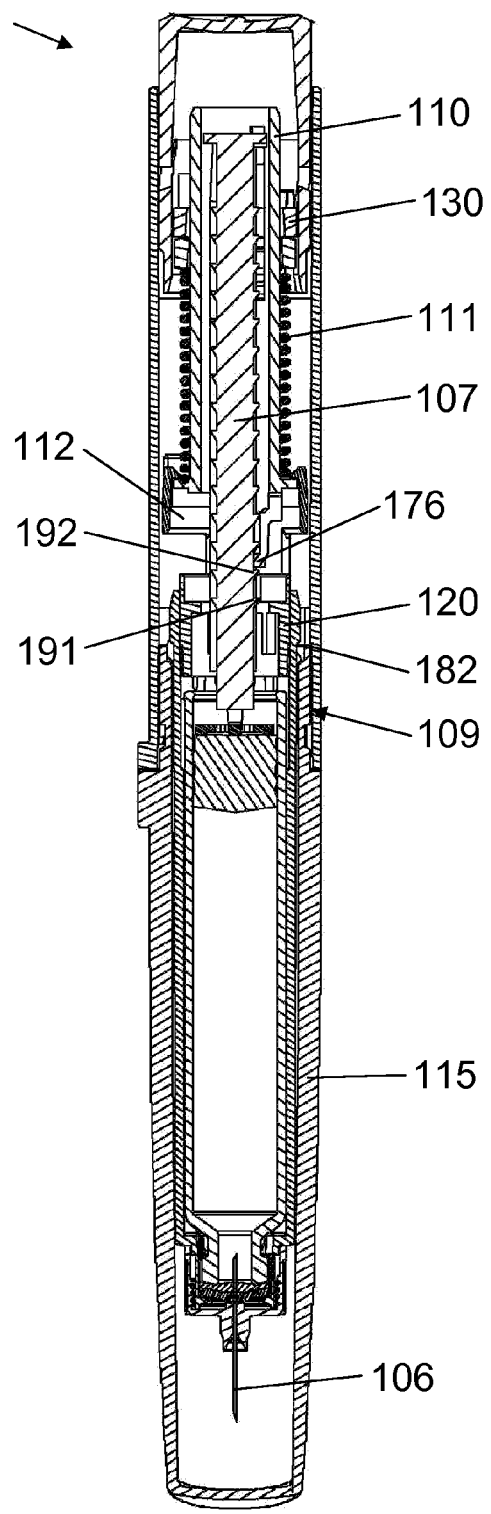
FIG. 4 is a cross sectional view of the injection device of FIG. 1 where the cap has been remounted and the device is loaded.

In FIG. 4 the cap 115 has been remounted on the injection device 100 at the cap receiving portion 109 and a dose has consequently been set. During the remounting the cap 115 abuts the push element 112 and moves the push element 112 proximally. Thereby the driver 110 is moved proximally and the spring 111 is compressed axially. The pawl 176 is lifted a distance proximally and is now positioned proximally of the next tooth 192 on the piston rod 107, a small clearance being provided between the two.

Figure 5:
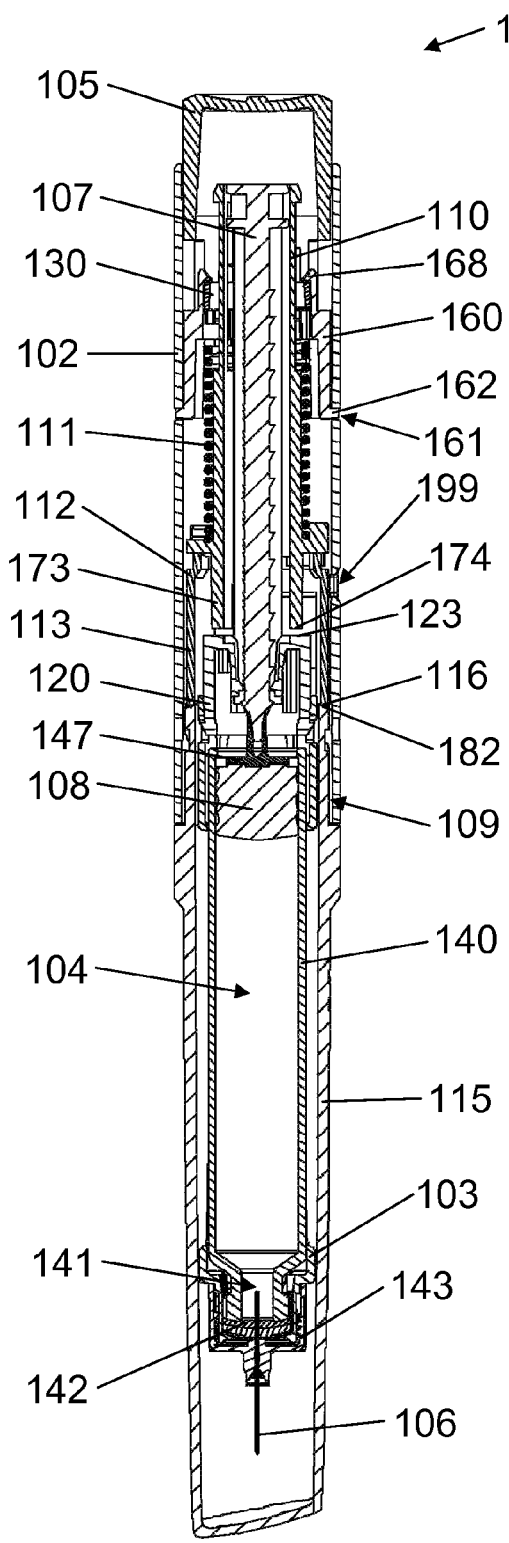
FIG. 5 is another cross sectional view of the injection device of FIG. 1, in a situation corresponding to FIG. 1.

FIG. 5 shows the injection device 100 in a different cross sectional view before the first injection, having the cap 115 mounted at the cap receiving portion 109. The cap 115 is held in the mounted position via a threaded interface (not visible) between the exterior surface of the cap 115 and the interior surface of the housing 102. The cap 115 has a round-going cap edge 182 which is in abutment with a couple of contact soles 116 on the push element 112. The cap edge 182 exerts a force on the contact soles 116 which is transferred via two legs 113 to the driver 110. As the driver 110 is in engagement with the spring 111 the driver 110 is biased by the spring 111 against the push element 112. The push element 112 is thus biased against the cap 115 when the cap 115 is mounted at the cap receiving portion 109.

The driver 110 comprises a couple of slide members 173 which are adapted to control the movements of the driver 110 through an interface with the guide member 120. In FIG. 5 the driver 110 is out of contact with the guide member 120. This is seen by a small clearance between contact soles 174 on the respective slide members 173 and a dose shelf 123 on the guide member 120.

FIG. 5 further shows a see-through window 199 in the housing 102 and apertures 161 which are occupied by hooks 162 providing a rotational and translational fixation of the spring base 160 relative to the housing 102. A couple of snap arms 168 lock the coupling ring 130 translationally to the spring base 160.

Figure 6:
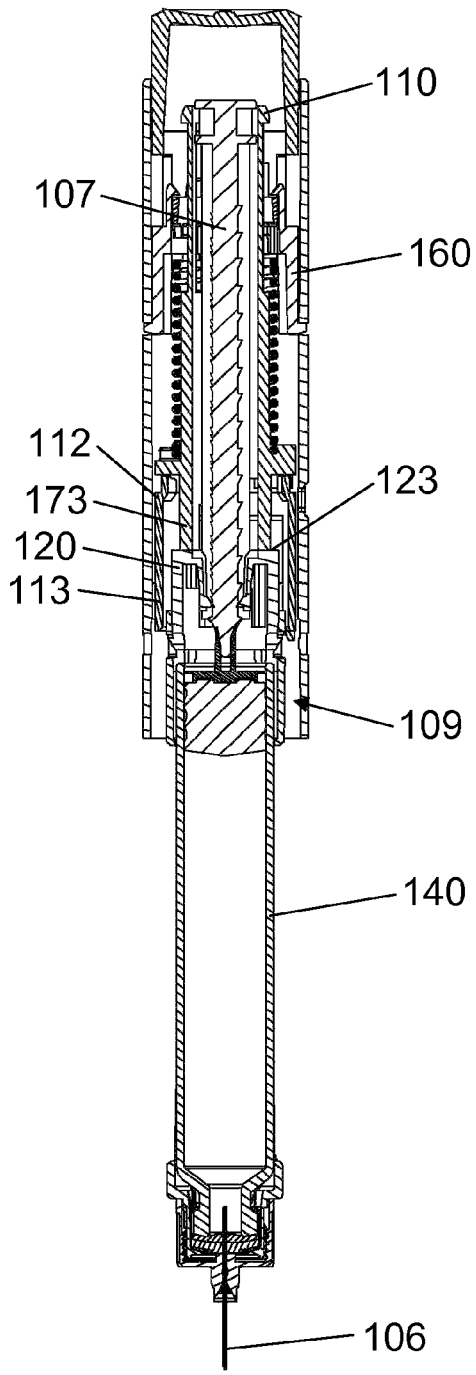
FIG. 6 is another cross sectional view of the injection device of FIG. 1, in a situation corresponding to FIG. 2.

FIG. 6 shows the injection device 100 after removal of the cap 115. It is seen that as a consequence of the dismounting of the cap 115 the spring 111 has forced the slide members 173 to move into abutment with the dose shelf 123.

Figure 7:
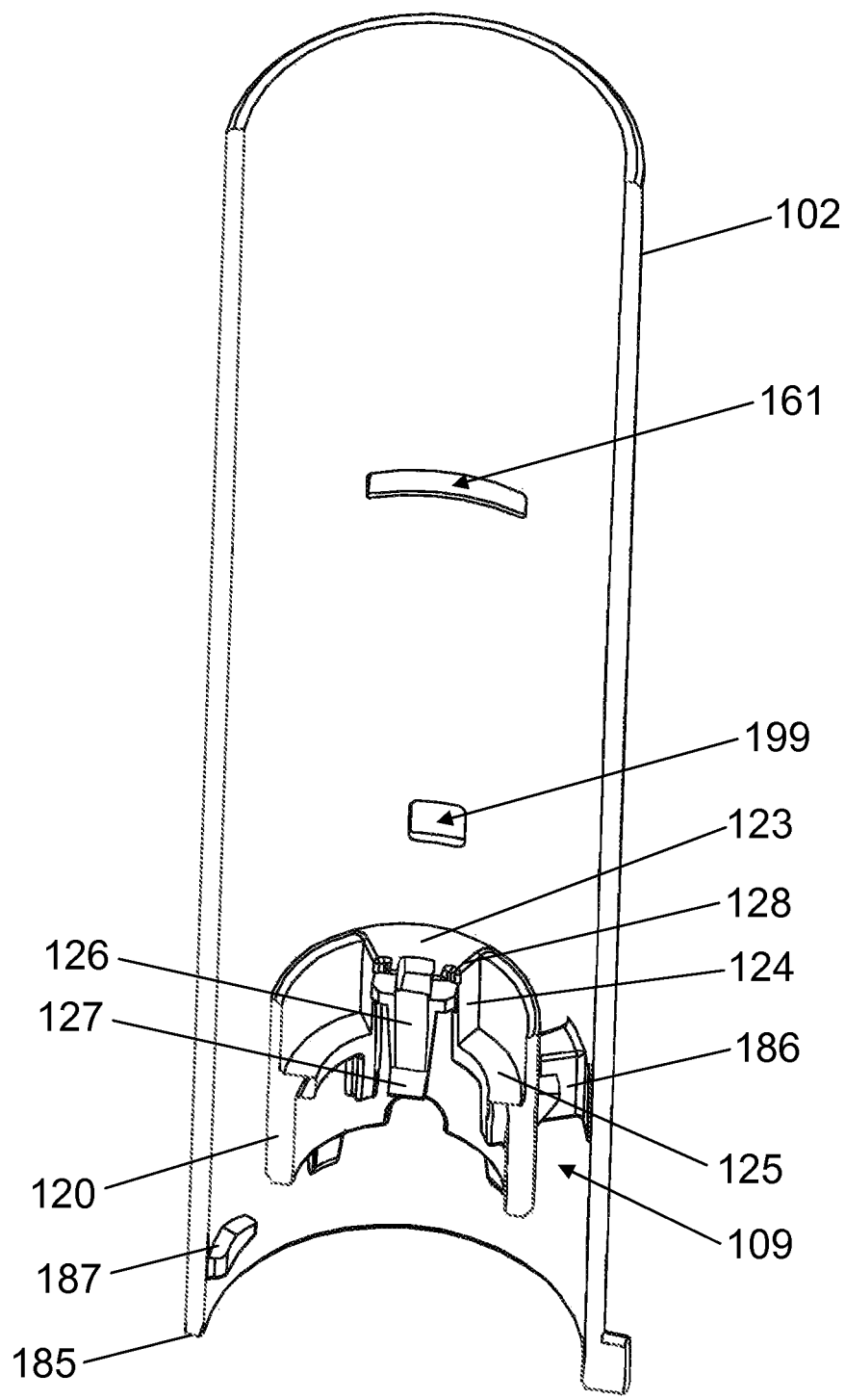
FIG. 7 is a cross sectional perspective view of a housing part, showing a guide means in detail.

FIG. 7 is a cross sectional perspective view of the housing 102, which shows the guide member 120 in more detail. For the sake of clarity the proximal end of the cartridge holding part 103 has been removed from the figure. The guide member 120 comprises the dose shelf 123 adapted to support the driver 110 after removal of the cap 115 from the cap receiving portion 109. A longitudinal guide surface 124 leads from an edge 128 of the dose shelf 123 to an end of dose stop 125. A couple of radially deflectable click fingers 126 are provided on the guide member 120 (only one is visible), each click finger 126 having a tip 127 for engagement with the piston rod 107. The guide member 120 is arranged concentrically in the housing 102 spaced apart from the housing 102 by a number of spacers 186. A protrusion 187 is provided near a distal housing edge 185 for engagement with a helical track segment on the cap 115. This engagement provides for an axial fixation of the cap 115 to the housing 102 when the cap 115 is mounted at the cap receiving portion 109.

Figure 8:
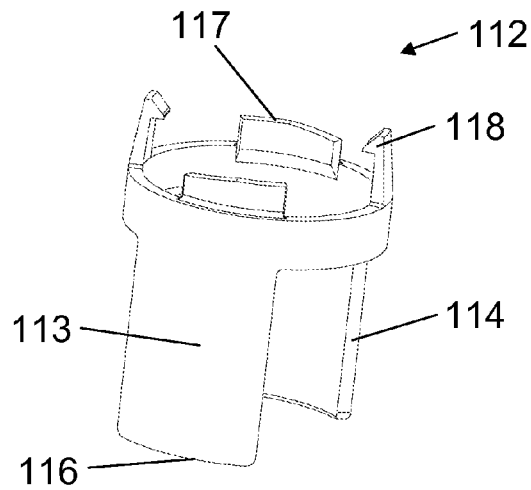
FIG. 8 is a perspective view of a push element used in the injection device of FIG. 1.

FIG. 8 is a perspective view of the push element 112, showing two helical guide segments 117 along which the driver 110 slides during dose setting. The legs 113 are positioned in the housing 102 between respective spacers 186 which thereby provide a rotational fixation of the push element 112 to the housing 102 through contacts with contact surfaces 114. The push element 112 is in this arrangement, however, able to move axially with respect to the housing 102.

Figure 9:
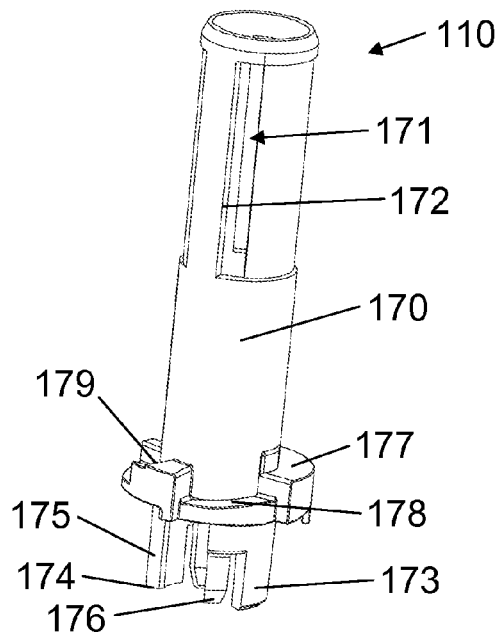
FIG. 9 is a perspective view of a drive member used in the injection device of FIG. 1, FIGS. 10a and 10b are different perspective views of a piston rod used in the injection device of FIG. 1.

FIG. 9 is a perspective view of the drive member 110, generally comprising a tubular body 170 having two radially opposed longitudinal slits 171 extending from its proximal end portion, each slit 171 neighbouring a longitudinal contact surface 172. A shoulder portion 177 connects the tubular body 170 with a distal portion which comprises two slide members 173 adapted to travel the guide surfaces of the guide member 120. The slide members 173 have respective slide surfaces 175 each interfacing with one of the longitudinal guide surfaces 124. The pawls 176 are rigidly connected to the slide members 173 such that the pawls 176 undergo the same translational and/or rotational movement as the slide members 173, and vice versa. The shoulder portion 177 provides a physical interface for the exchange of axial forces between the spring 111 and the driver 110. A spring retaining section 179 provides a physical interface for the exchange of torques between the spring 111 (not shown) and the driver 110. Helical tracks 178 are adapted to interface with the snap arms 118 on the push element 112 and to enable a rotational motion of the driver 110 with respect to the push element 112.

Figure 10A:
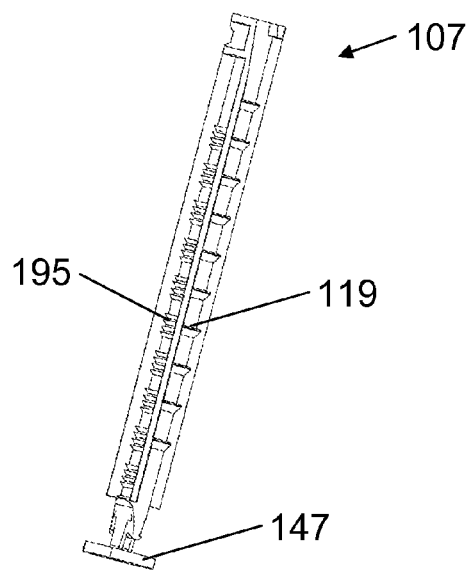

FIG. 10a is a perspective view showing two sides of the piston rod 107. A number of teeth 119 are distributed along the piston rod 107 on the first side, the distance between two consecutive teeth 119 being constant throughout the entire distribution. The teeth 119 are adapted for engagement with the driver 110 during dose injection where the pawl 176 engages a tooth 119 and slaves the piston rod 107 in a forward motion. Further, on the second side, clusters of smaller teeth 195 are evenly distributed along the piston rod 107. During an injection the tip 127 of one of the click fingers 126 rides over the teeth 195 thereby providing an audible confirmation of the progression of the injection.

Figure 10B:
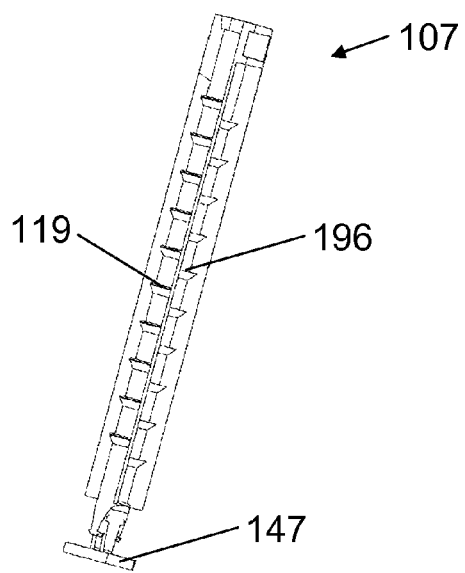

FIG. 10b is a perspective view showing the other two sides of the piston rod 107. On the third side, opposite to the first side, a number of teeth 119 are distributed in a way similar to the distribution on the first side. On the fourth side a number of teeth 196 are distributed, the teeth 196 being smaller than the teeth 119 but larger than the teeth 195. The distance between two consecutive teeth 196 equals the distance between two consecutive teeth 119 on the first and the third side of the piston rod 107. However, the teeth 196 are axially offset from the teeth 119. At the end of an injection the tip 127 of the other click finger 126 rides over a tooth 196 to provide an audible confirmation of the dose completion. Since the teeth 196 are larger than the teeth 195 the click provided when the click finger 126 overrides a tooth 196 is audibly distinguishable from the click provided when the other click finger 126 overrides a tooth 195. The teeth 196 and the click finger tip 127 are arranged so as to provide a ratchet and pawl mechanism preventing proximal movement of the piston rod 107 relative to the guide member 120.

Figure 11:
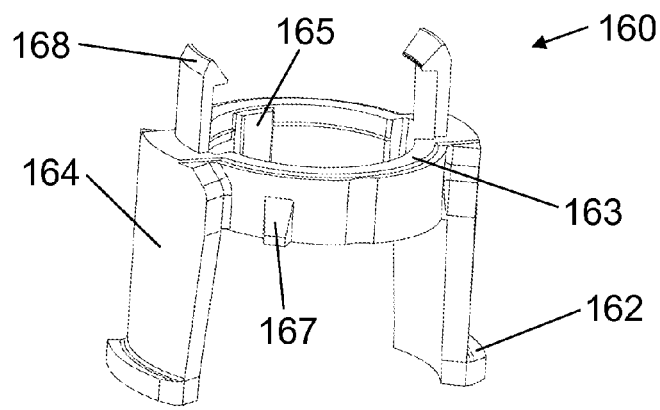
FIG. 11 is a perspective view of a spring holding element used in the injection device of FIG. 1.

FIG. 11 is a perspective view of the spring base 160 which is adapted to hold one end of the spring 111 in a permanent position with respect to the housing 102. The spring base 160 has two radially opposed arms 164 each comprising a hook 162 for engagement with the respective apertures 161 in the housing 102. Due to the engagement between the hooks 162 and the apertures 161 the spring base 160 is completely locked to the housing 102, i.e. the spring base 160 is prevented from performing rotational as well as translatory motion relative to the housing 102. A boss member 165 is provided for retaining the proximal end of the spring 111 and for limiting the axial movements of the driver 110. The spring base 160 further comprises a proximal face 163 adapted to abut with the coupling ring 130, and a pair of snap arms 168 fixing the coupling ring 130 axially with respect to the spring base 160. A projection 167 is also provided for interfacing with the injection button 105.

Figure 12:
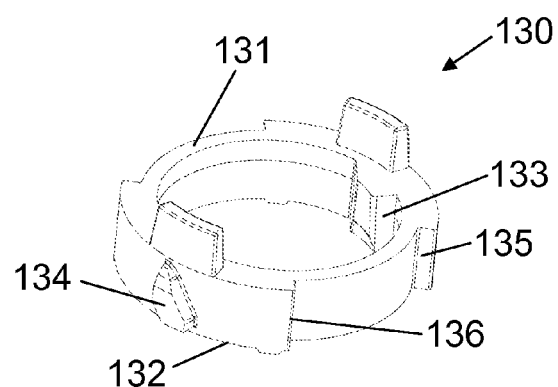
FIG. 12 is a perspective view of a coupling element used in the injection device of FIG. 1.

FIG. 12 is a perspective view of the coupling ring 130 adapted to couple the injection button 105 with the driver 110. The coupling ring 130 has a proximal face 131 and a distal face 132, and two radially opposed protuberances 133 adapted to interact with the contact surfaces 172 on the tubular body 170 of the driver 110 to provide for a rotational master-slave relationship between the coupling ring 130 and the driver 110. During use the protuberances 133 and the contact surfaces 172 are in pair-wise abutment such that when the coupling ring 130 is rotated clockwise the driver 110 is forced to rotate clockwise and when the driver 110 is rotated counter-clockwise the coupling ring 130 is forced to rotate counter-clockwise. The distal face 132 of the coupling ring 130 is adapted to abut with the proximal face 163 of the spring base 160, and the proximal face 131 of the coupling ring 130 is adapted to be engaged by the snap arms 168, i.e. the coupling ring 130 is axially fixed to the spring base 160. The coupling ring 130 and the driver 110 are able to perform relative translatory motion limited by the length of the slits 171. Two protrusions 134 are provided for coupling with the injection button 105. Further, the material thickness of the coupling ring 130 varies circumferentially to provide for a rotational play of the coupling ring 130 in relation to the spring base 160. In that respect, the snap arms 168 will be able to slide between respective walls 135 and 136 when the coupling ring 130 rotates relative to the spring base 160.

Figure 13:
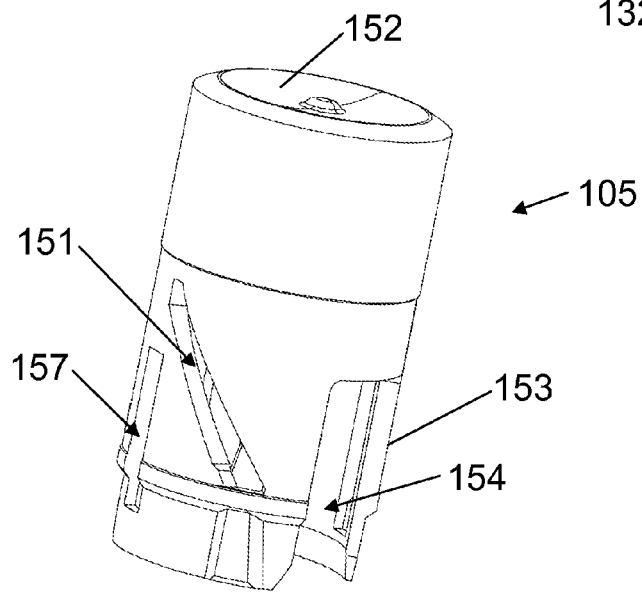
FIG. 13 is a perspective view of an injection button used in the injection device of FIG. 1.

FIG. 13 is a perspective view of the injection button 105 comprising a push face 152 for interfacing with an operator of the injection device 100. The injection button 105 further comprises two flanges 153, each provided with a helical track 151 and a longitudinal slit 157. The helical tracks 151 are adapted to interface with the respective protrusions 134 to transform a translational motion of the injection button 105 to a rotational motion of the coupling ring 130, and vice versa. Further, two clearances 154 are provided for interfacing with the respective arms 164, thereby allowing translational motion of the injection button 105 relative to the spring base 160 while preventing rotational motion of the injection button 105 relative to the spring base 160. As the spring base 160 is rotationally fixed relative to the housing 102 the injection button 105 is only allowed to move translationally with respect to the housing 102. The longitudinal slits 157 are adapted to slidably occupy the respective projections 167. The translational motion of the injection button 105 relative to the spring base 160 is therefore limited in the proximal direction by the interaction between the projections 167 and the respective distal ends of the longitudinal slits 157 and in the distal direction by the interaction between the respective proximal ends of the arms 164 and the respective proximal ends of the clearances 154.

FIG. 14 is a perspective view showing an assembly of the driver 110, the spring 111, the coupling ring 130, the spring base 160, and the piston rod 107. In particular, FIG. 14 shows the axially fixed coupling between the coupling ring 130 and the spring base 160.

FIG. 15 is a perspective view showing an assembly of the injection button 105, the driver 110, the spring 111, the coupling ring 130, the spring base 160, the push element 112, and the piston rod 107, and illustrating the functional connection between the injection button 105 and the driver 110. The figure shows the injection button 105 fully depressed against the spring base 160, i.e. in a position corresponding to a dose having just been injected. The proximal spring end (not visible) is retained in the spring base 160 and the distal spring end is in connection with the driver 110 at the spring retaining section 179. As the spring base 160 is locked to the housing 102 and thereby unable to move the torsionally pre-tensioned spring 111 will bias the driver 110 counter-clockwise, as seen from the injection button 105.

During the injection procedure a push on the push face 152 forces the injection button 105 downwards towards the spring base 160. As the injection button 105 is locked against rotation relative to the spring base 160 this downwards movement is purely translational. During the translational movement of the injection button 105 the protrusions 134 travel the helical tracks 151. This engagement converts the movement of the injection button 105 to a rotational movement of the coupling ring 130, and since the coupling ring 130 is rotationally engaged with the driver 110, the driver 110 will also rotate. The helical tracks 151 are arranged such that when the injection button 105 is pushed towards the spring base 160 the coupling ring 130, and thereby the driver 110, will rotate clockwise, as seen from the injection button 105, i.e. against the rotational bias of the spring 111.

FIG. 16 is a two-dimensional representation of the movement patterns of the respective slide members 173 and the piston rod 107 relative to each other and relative the guide member 120 in the housing 102 during priming, injection and loading of the injection device 100. The representation in FIG. 16 presupposes that the contact soles 174 of the slide members 173 and the pawls 176 are axially aligned with respect to the housing 102. This may not necessarily be the case. However, that specific construction of the driver 110 is adopted here for the sake of clarity. It is understood that the guide member 120 comprises two sets of guiding surfaces which the two slide members 173 travel simultaneously. However, as this movement of the slide members 173 along the respective guiding surfaces is identical only one of them is presented. The various movements will be described in detail below.

Figure 17:
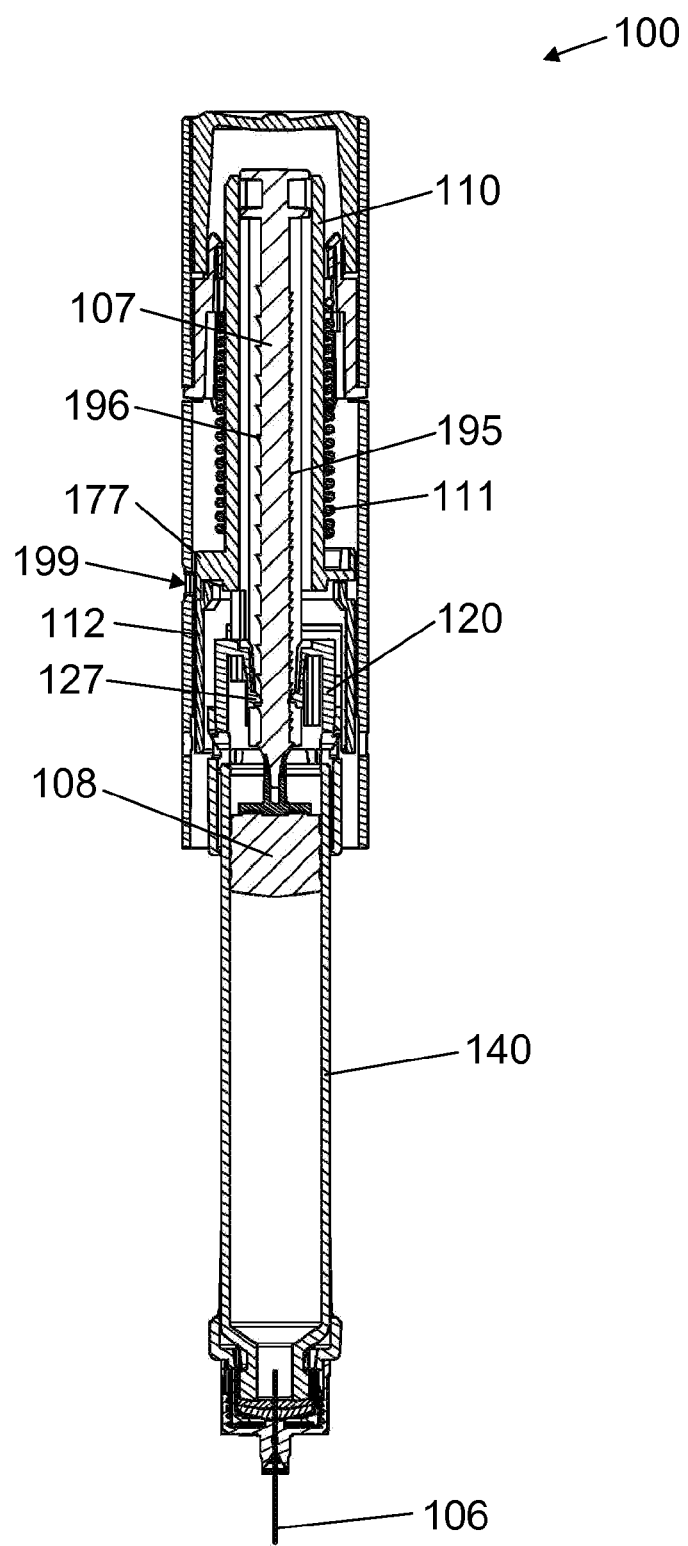
FIG. 17 is a cross sectional view of the injection device of FIG. 1 in an end-of-dose situation, where the drive member is viewable through a window in the housing.

FIG. 17 is a cross sectional view of the injection device 100 following an injection. It is seen that whereas the legs 113 of the push element 112 were visible through the window 199 in FIGS. 7 and 8, the shoulder 177 of the driver 110 is now visible. The interface between the push element 112 and the driver 110 is arranged such that the driver 110 becomes visible through the window 199 only at the point where an injection has been fully completed, i.e. at the point where the entire set dose of drug is expelled from the cartridge 104. The driver 110 has a different colour than the push element 112 so the user is able to check through the window if the desired dose has in fact been delivered. If the window is not completely filled with the colour of the driver 110 a few seconds after the user has pressed down the injection button 105 it is an indication that an obstruction to the delivery has occurred and that the dose is incomplete. In this embodiment the driver 110 is green and the push element 112 is black. However, any combination of colours for the two structural elements can be envisioned, as long as they are visibly distinguishable.

In FIG. 17 it is also seen that the tip 127 of the click finger 126 has just passed an end-of-dose click tooth 196 which has further provided an audible indication of the dose completion. Thereby, two different end-of-dose indicators are provided, a short-lived audible click and a lasting visual colour change, enhancing the safety of the user.

Figure 18A:
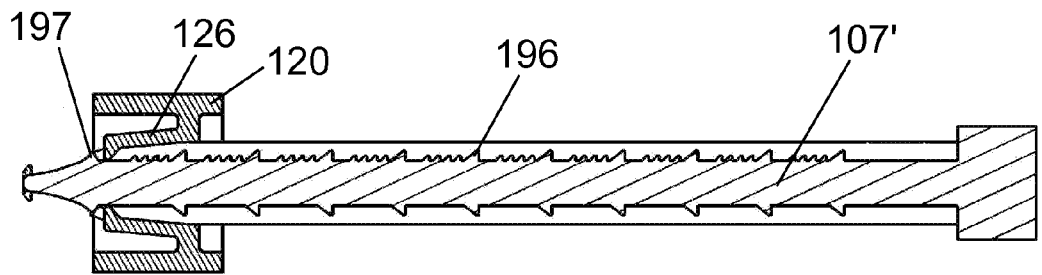
FIG. 18a-c are cross sectional views of an embodiment of a surpassable one-way mechanism in the injection device.
Figure 18B:
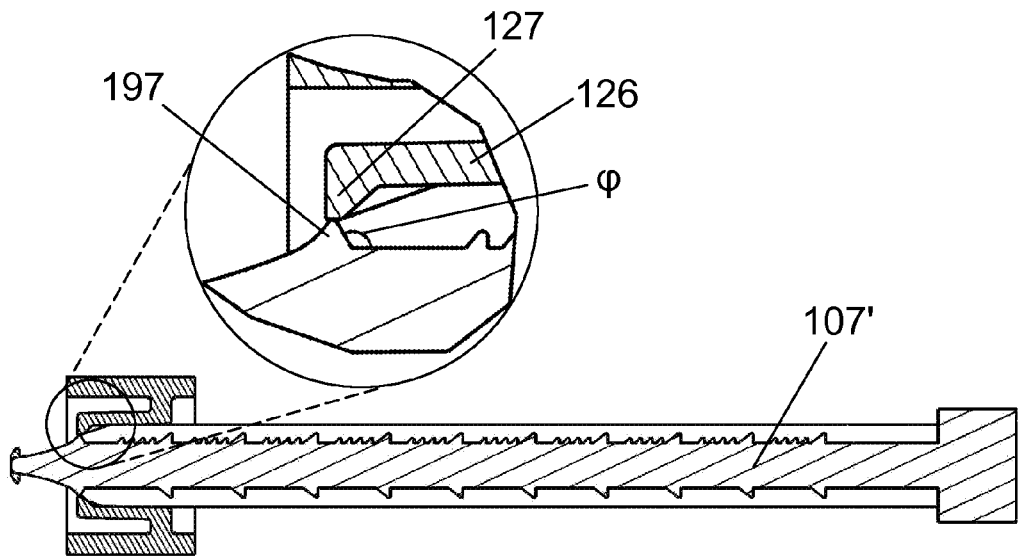
Figure 18C:
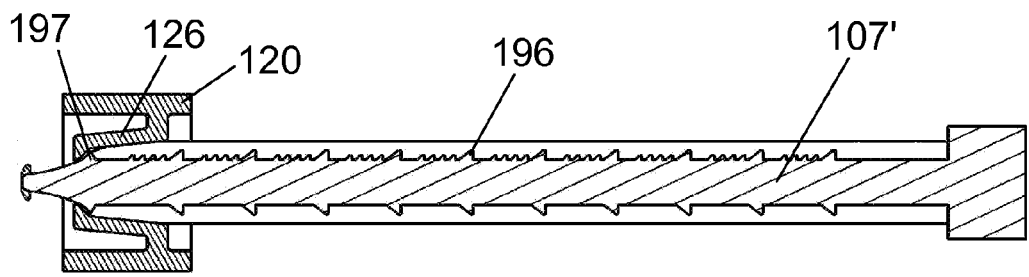

FIG. 18a-c show cross sectional views of a coupling between the guide member 120 and a piston rod 107'. The piston rod 107' is similar to the piston rod 107 shown in relation to the injection device of FIG. 1, the only difference being that the piston rod 107' is provided with end of dose click teeth 196 on two sides. FIG. 18a shows a distal most, or start, position of the piston rod 107' relative to the guide member 120. This position corresponds to a situation where the injection device has not yet been used, i.e. before the first dose has been injected. A couple of front teeth 197 are situated distally of the click fingers 126 providing a limit to the axial displacement of the piston rod 107' in the proximal direction. The piston (not shown) provides, via the piston rod foot (also not shown), a limit to the axial displacement of the piston rod 107' in the distal direction. The respective proximally facing surfaces of the teeth 197 are at an obtuse angle, cp, (best seen in FIG. 18b) to the surface of the body of the piston rod 107' and at an acute angle to the distally facing surfaces of the respective tips 127. This arrangement provides for a one-way coupling between the piston rod 107' and the housing 102 that is surpassable only when the piston rod 107' is subjected to forces above a certain threshold value. As long as the proximally, or backward, directed force on the piston rod 107' is lower than the threshold value the engagement between the teeth 197 and the tips 127 prevent backward movements of the piston rod 107'. However, if the force becomes greater than the threshold value, e.g. as a consequence of the drug freezing and expanding in the cartridge 104, thereby exerting a large backward directed pressure on the piston 108, the click fingers 126 will deflect radially and allow the piston rod 107' to displace proximally with respect to the guide member 120. This is seen in FIG. 18b. In FIG. 18c the tips 127 have completely passed the teeth 197 and the piston rod 107' is free to travel further backwards with respect to the guide member 120. The click finger 126 has elastically recovered to its original unstressed position.

Figure 19A:
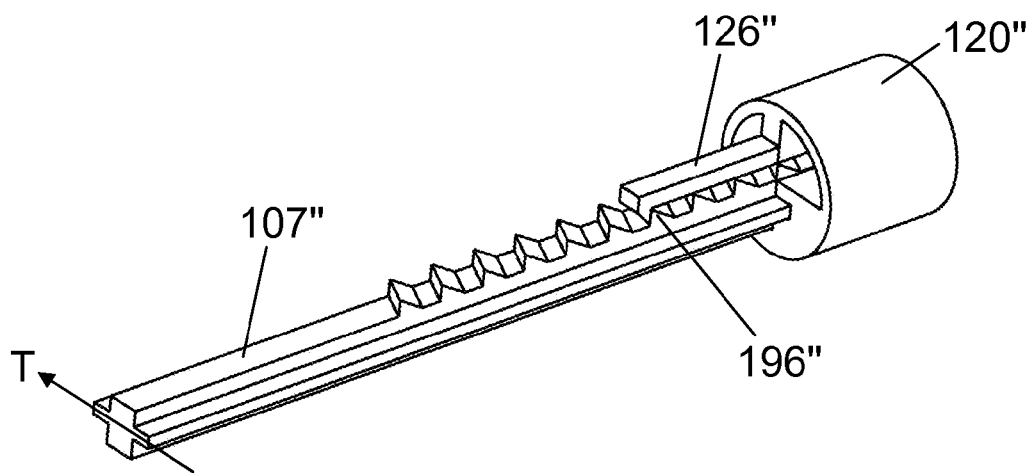
FIGS. 19a and 19b are perspective views of another embodiment of a surpassable one-way mechanism in the injection device.

FIG. 19a shows a different design of a one-way coupling between the piston rod and the housing. In this embodiment a guide member 120", having the same general features as the guide member 120 described in the above except from a different click finger 126" arrangement, and a piston rod 107", having the same general features as the piston rod 107 described in the above except from a different end of dose click tooth 196" arrangement, are shown in a situation where the piston rod 107" is prevented from moving backwards (to the left in the figure) relative to the guide member 120" due to an engagement between the click finger 126" and a tooth 196". The teeth 196" are skewed, i.e. they are angled relative to the transverse axis, T, of the piston rod 107". As long as the backward directed force on the piston rod 107" is lower than a certain threshold value the engagement between the click finger 126" and the tooth 196" is sufficient to prevent the piston rod 107" from moving backwards relative to the guide member 120".

Figure 19B:
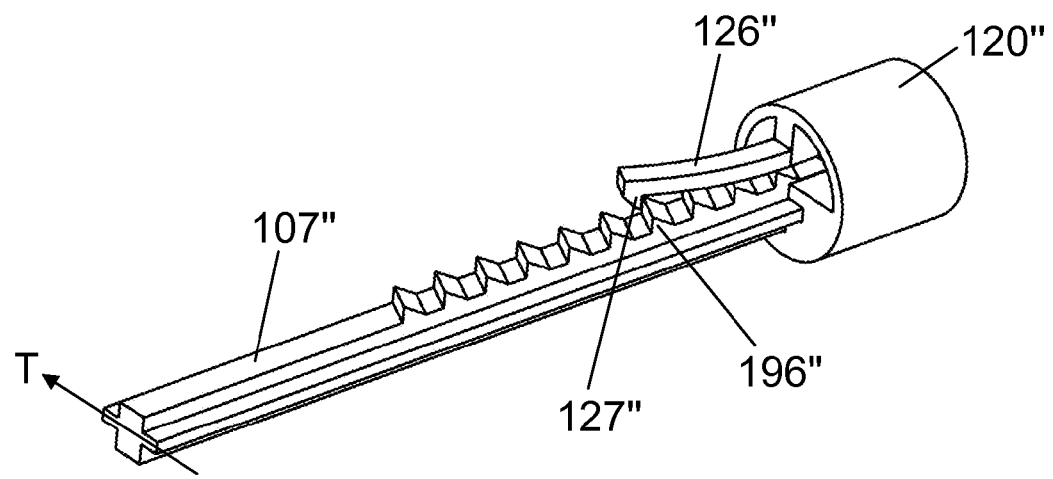

FIG. 19b shows the arrangement of FIG. 19a in a situation where the backward directed force on the piston rod 107" has surpassed the threshold value. This has caused the click finger 126" to deflect sideways, whereby a tip 127" has travelled the skewed tooth surface and finally broken the engagement between the tooth 196" and the click finger 126" to allow for a backward movement of the piston rod 107" relative to the guide member 120". Once the tooth 196" has passed the click finger 126", the click finger 126" will recover elastically to its original position parallel to the longitudinal axis of the piston rod 107".

In the following a situation of use of the injection device 100 will be described.

The injection device 100 shown in FIGS. 1 and 5 is in a non-use state having the cap 115 mounted thereon. As long as the cap 115 is mounted on the injection device 100 at the cap receiving portion 109 it contacts the contact soles 116 of the push element 112 via the cap edge 182 and prevents the push element 112 from moving axially in a distal direction. The push element 112 is in abutment with the driver 110 so the axial position of the push element 112 determines the axial position of the driver 110 in the housing 102. When the cap 115 is mounted at the cap receiving portion 109 the contact soles 174 of the driver 110 are lifted proximally away from the dose shelves 123 of the guide member 120. In this position the cap 115 prevents axial movements of the driver 110 in the distal direction against the bias of the spring 111 which is axially compressed and which exerts a distally directed force on the driver 110. The pawls 176 are spaced apart from the respective teeth 191, resulting in a small clearance between the driver 110 and the piston rod 107.

When the user needs to perform an injection he removes the cap 115 from the injection device 100. If an injection needle 106 is mounted at the needle hub interface 143 the following will happen. The proximally directed force on the push element 112 from the cap 115 is removed and the spring 111 is released and will move the driver 110 in the distal direction until the contact soles 174 of the slide members 173 reach the dose shelves 123. When this happens the driver 110 is brought to a stop and the spring 111 is retained in a new, slightly less compressed state. Due to the rigid construction of the driver 110 the movement of the slide members 173 is reflected directly on the pawls 176 which move a corresponding distance in the distal direction. At some point during this movement the pawls 176 will engage with the pair of teeth 191 and slave the piston rod 107 a small distance. As can be seen from FIG. 16 a removal of the cap 115 from the cap receiving portion 109 results in a distal movement, D, of the slide members 173, and thereby of the driver 110 and the pawls 176. The engagement of the pawls 176 and the teeth 191 (shown as the tooth 192 in FIG. 16 for the sake of clarity) occurs when the driver 110 has moved a distance D-E, and the resulting distal movement of the teeth 191 (the tooth 192 in FIG. 16), and thereby of the piston rod 107, is E.

If there is no initial slack between the piston rod foot 147 and the piston 108 the entire movement of the piston rod 107 will be transferred to the piston 108, i.e. the piston 108 will be displaced the distance E. If there, however, is an initial slack, δ (not shown), between the piston rod foot 147 and the piston 108, then the displacement of the piston 108 will be E−δ.

In any case, a dismounting of the cap 115 from the cap receiving portion 109 will result in an automatic advancement of the piston 108 in the cartridge 104, causing a small volume of the drug to be expelled through the injection needle 106. Having thus automatically de-aerated the injection needle 106 and secured proper abutment between the piston rod foot 147 and the piston 108 the injection device 100 is ready to be used for injection of a dose of the drug.

The user inserts the injection needle 106 through the skin and applies a force to the push face 152 to press the injection button 105 down towards the housing 102. This will result in a purely translatory distal movement of the injection button 105 with respect to the housing 102 until the proximal ends of the arms 164 of the spring base 160 and the proximal ends of the clearances 154 abut. During this movement of the injection button 105 the projections 167 travel the longitudinal slits 157 from a position at the respective distal ends of the longitudinal slits 157 to a position at the respective proximal ends of the longitudinal slits 157. Further, the protrusions 134 travel the helical tracks 151, also in the proximal direction. Since the injection button 105 is rotationally fixed with respect to the housing 102 this movement of the protrusions 134 along the helical tracks 151 will result in a clockwise rotation of the coupling ring 130 with respect to the spring base 160. Due to the rotational master-slave relationship between the coupling ring 130 and the driver 110 the rotation of the coupling ring 130 is directly transferred to the driver 110. Hence, the driver 110 is rotated clockwise against the rotational bias of the spring 111 acting at the spring retaining section 179.

As the driver 110 rotates relative to the housing 102, it also rotates relative to the push element 112 and the guide member 120. The slide members 173 slide along the dose shelves 123 until they reach the edges 128. When the slide members 173 pass the edges 128 the spring 111 is released from its axial retention and forces the driver 110 in the distal direction whereby the slide members 173 travel the longitudinal guide surfaces 124 until they reach the end of dose stops 125. Both during the movement of the slide members 173 along the longitudinal guide surfaces 124 and when the slide members are positioned at the end of dose stops 125 they are biased against the longitudinal guide surfaces 124 due to the torsional tension in the spring 111 biasing the driver 110 in the counter-clockwise direction. This means that when the driver 110 is in the end of dose position it is unable to rotate with respect to the housing 102. Since the driver 110 is unable to rotate with respect to the housing 102, so is the coupling ring 130, and since the coupling ring 130 is unable to rotate with respect to the housing 102 the injection button 105 is forced to maintain its axial position relative to the housing 102. In other words, once the user has activated the injection mechanism the injection button 105 stays depressed against the housing 102.

During the distal movement of the driver 110 the piston rod 107, being slaved by the pawls 176, and thereby the piston 108, is displaced a distance H (see FIG. 16), corresponding to the desired volume of drug to be delivered to the user. The displacement of the piston rod 107 relative to the housing 102 causes one of the click fingers 126 to override a cluster of teeth 195, thereby providing an audible indication to the user that the injection is in fact progressing. In the course of a dose delivery the piston rod 107 is thus displaced a total distance of A, equalling E+H. The piston rod 107, the driver 110, and the guide member 120 are relatively positioned and configured such that E is much smaller than H, i.e. the priming dose is at any time only a fraction of the therapeutic dose.

When the driver 110 moves in the distal direction in the housing 102 it pushes the push element 112 in the same direction. Initially, and as long as the injection is on-going, the push element 112 is visible to the user when he looks through the window 199. However, at exactly the point where the slide members 173 move into abutment with the end of dose stops 125 the driver 110 pushes the push element 112 completely past the window 199, whereby only the driver 110 will be visible to the user when he looks through the window 199. As the driver 110 is green and the push element 112 is black the colour in the window 199 changes when the dose is complete, indicating to the user that the injection has been unobstructed. At the same time the tip 127 of the click finger 126 rides over the end of dose click tooth 196 providing an audible click sound which also indicates to the user that the dose has been carried through.

If an injection needle is not mounted at the needle hub interface 143 when the user removes the cap 115, the driver 110 will be forced in the distal direction by the spring 111 until the pawls 176 engage with the teeth 191 and the piston rod foot 147 is in abutment with the piston 108. Provided there is no initial slack between the piston rod foot 147 and the piston 108 the distal movement of the driver 110 is D–E (see FIG. 16). If there is an initial slack, δ (not shown), between the piston rod foot 147 and the piston 108 then the distal movement of the driver 110 is D–E+δ. In any case the piston rod 107 will exert a pressure on the piston 108 via the piston rod foot 147, but the piston 108 will not move due to the incompressibility of the contents of the cartridge 104. The cartridge 104 remains pressurised, however, due to the spring 111 exerting a constant force on the driver 110, until the user attaches an injection needle 106 to the needle hub interface 143. When the injection needle 106 penetrates the septum 142 the excess pressure in the cartridge 104 is relieved resulting in the spring 111 being able to push the driver 110 further distally until the slide members 173 reach the dose shelves 123. At this point the driver 110 is brought to a stop and the spring 111 is retained in a new, slightly less compressed state. Like in the above described situation this causes the piston 108 to be displaced either a distance E (if there is no initial slack between the piston rod foot 147 and the piston 108) or a distance E–δ (if there is an initial slack between the piston rod foot 147 and the piston 108), leading to a small volume of drug being expelled from the cartridge 104. The injection device 100 has now been automatically primed and a subsequent injection procedure will be identical to the one described in the above.

Remounting of the cap 115 onto the cap receiving portion 109 after an injection will cause a next dose to be set, as explained in the following.

At some point during the remounting of the cap 115 onto the cap receiving portion 109 the cap edge 182 will abut the contact soles 116 of the legs 113, and as the cap edge 182 is moved gradually further towards the proximal end of the injection device 100 the push element 112 will accordingly displace proximally. This proximal displacement of the push element 112 will cause a proximal displacement of the driver 110 against the axial bias of the spring 111. Thereby, the driver 110 is pushed away from the window 199 and the slide members 173 travel the longitudinal guide surfaces 124 from the end of dose stops 125 towards the edges 128. When the slide members 173 have travelled the distance H and reach the edges 128 the rotational bias of the spring 111 will force the driver 110 to rotate counter-clockwise with respect to the housing 102. During this rotation the driver 110 will slide along the helical guide segments 117 on the push element 112. When the driver 110 travels the helical guide segments 117 the pawls 176 are moved a distance D proximally from a position just below the next pair of teeth 192 to a position a little above the teeth 192 in a combined translatory and rotational motion. A small clearance is thereby introduced between the pawls 176 and the teeth 192 (the axial length of the clearance depending on whether or not the loading process has introduced a slack between the piston rod foot 147 and the piston 108).

The counter-clockwise rotation of the driver 110 results in an equal counter-clockwise rotation of the coupling ring 130 due to the engagement between the contact surfaces 172 and the protuberances 133. The rotation of the coupling ring 130 leads to a translatory movement of the injection button 105 in the proximal direction out of the housing 102 due to the interaction between the protrusions 134 and the helical tracks 151. The thereby caused axial movement of the injection button 105 is limited by the travel of the projections 167 in the longitudinal slits 157. When the projections 167 reach the distal ends of the longitudinal slits 157 the movement of the injection button 105 is stopped as the injection button 105 is unable to protrude any further from the housing 102. The rotation of the coupling ring 130 is therefore also stopped, and so is the rotation of the driver 110. The spring 111 is now retained rotationally in the original pre-stressed state.

In the following the function of the surpassable one-way coupling between the piston rod 107' and the guide member 120, as shown in FIG. 18a-c, and its relation to the frost protected injection mechanism will be described in further detail. Hence, the following description assumes that the injection device 100 comprises the piston rod 107' instead of the piston rod 107.

In FIGS. 1 and 5 the injection device 100 is in a storage situation before the first use. The pawls 176 are positioned proximally of the distal most teeth 191 and the click fingers 126 are positioned proximally of the front teeth 197. If the injection device 100 is being transported or otherwise put through rough handling the piston rod 107' is prevented from moving proximally in the housing 102 beyond the point of engagement between the teeth 197 (depicted for example in FIGS. 18a-18 c)and the click fingers 126 as long as this engagement is able to withstand forces of certain relatively low values.

However, if the injection device 100 is subjected to a temperature below the drug's freezing point, e.g. if placed next to a highly active cooling element in a refrigerator, the drug will freeze and expand the cartridge 104. This will lead to a proximal, or backwards, directed pressure on the piston 108 which will cause a proximal displacement of the piston 108 in the cartridge 104. If there is no slack between the piston 108 and the piston rod foot 147 this will lead directly to a backward directed force of a significant size being applied to the piston rod 107'. If there is a slack between the piston 108 and the piston rod foot 147 the two will firstly be forced together. The piston 108 will then cause the piston rod 107' to apply a backward directed force to the click fingers 126 via the contact interface between the teeth 197 and the tips 127. Due to the fact that the respective proximally facing surfaces of the teeth 197 are at the obtuse angle φ to the body of the piston rod 107' the click fingers 126 will deflect radially outwards, i.e. towards the inner surface of the guide member 120, and slide along the teeth 197 until the piston rod 107' has moved sufficiently backwards to enable the tips 127 to pass the edges of the teeth 197. After having passed the edges of the teeth 197 the click fingers 126 will elastically recover to their original radial positions and slide freely along the distally facing surfaces of the teeth 197. The piston rod is thereby no longer in locking engagement with the guide member 120 and can move further backwards until the distal most teeth 191 are brought into engagement with the pawls 176 of the driver 110.

The unidirectional interface between the teeth 191 and the pawls 176 prevent the piston rod 107' from moving further backwards with respect to the driver 110. However, as the driver 110 is able to move axially backwards in the housing 102 due to the longitudinal slits 171 the force is merely transmitted to the driver 110, whereby the driver 110 and the piston rod 107' move concurrently backwards against the axial bias of the spring 111.

At some point the backward directed force on the driver 110 originating from the expanding drug in the cartridge 104 and the forward directed biasing force on the driver 110 from the compressed spring 111 will reach an equilibrium condition, whereby the driver 110 and the piston rod 107' are halted. The driver 110 and the piston rod 107' will remain in this position until the drug thaws again. When this happens the pressure on the piston 108 is relieved and consequently the force transmitted to the piston rod 107' and the driver 110 is removed. The compressed spring 111 will then simply return the driver 110 to its original axial position defined by the cap edge 182 and the push element 112, and the driver 110 will during this return movement slave both the piston rod 107' and the piston 108. The elastically recovering piston rod drive arrangement thus ensures that the injection device 100 is not damaged even though the piston 108 forces the piston rod 107' backwards in the housing 102. Further, as the piston rod 107' is returned to an operational position from which it will be biased and/or displaced towards the piston 108 exactly as originally intended when the cap 115 is dismounted from the cap receiving portion 109, the low temperatures have not caused any reduction in the dose accuracy of the injection device 100.

It is noted that the injection device 100 incorporating the piston rod 107' could just as well incorporate the piston rod 107 having end of dose click teeth 196 on just one of its sides without affecting the general functionality of the described one-way coupling mechanism.

It is also noted that even though only the front teeth 197 are shown provided with an obtuse-angled tooth surface it is clear that the end of dose click teeth 196 can be arranged in a like manner, thereby enabling a surpassable one-way coupling between the piston rod 107 and the housing 102 at any point of engagement between the click fingers 126 and the teeth 196. This may be relevant to ensure that e.g. frictional forces between the driver 110 and the piston rod 107 during a dose setting, where the pawls 176 slide along the piston rod 107 and override a pair of teeth 119, will not move the piston rod 107 relative to the guide member 120, while still allowing for an axial displacement of the entire piston rod drive in response to forces of or above the threshold value.

Experiments conducted in relation to the present invention have shown that during transport and general handling of the injection device 100, including the setting of a dose, the piston rod 107 may be subjected to proximally directed forces of a magnitude of up to 2-5 N, whereas as a consequence of the liquid drug freezing in the cartridge 104 the piston rod 107 may be subjected to forces in the range of 200-250 N. The surpassable one-way coupling should thus be able to resist forces of up to at least 5 N and at the same time allow for a displacement of the piston rod drive due to forces around 200 N. The interface between the respective teeth 196, 197 and the tips 127 of the click fingers 126 can be designed to allow for a reversible disengagement of the one-way coupling between the piston rod 107 and the guide member 120 at virtually any relevant axial force. The frictional relationship between the respective teeth 196, 197 and the tips 127 is decisive for when the disengagement occurs, i.e. the angle φ is one parameter to adjust for obtaining a desired threshold value for disengagement.

In order to achieve a certain safety margin for backward movements of the piston rod 107 in response to forces originating from normal transportation and use of the injection device 100, the angle φ can be chosen such that disengagement occurs when the backward directed force is about 15-25 N. This would correspond approximately to an angle φ of about 110-130 degrees.

Figure 20A:
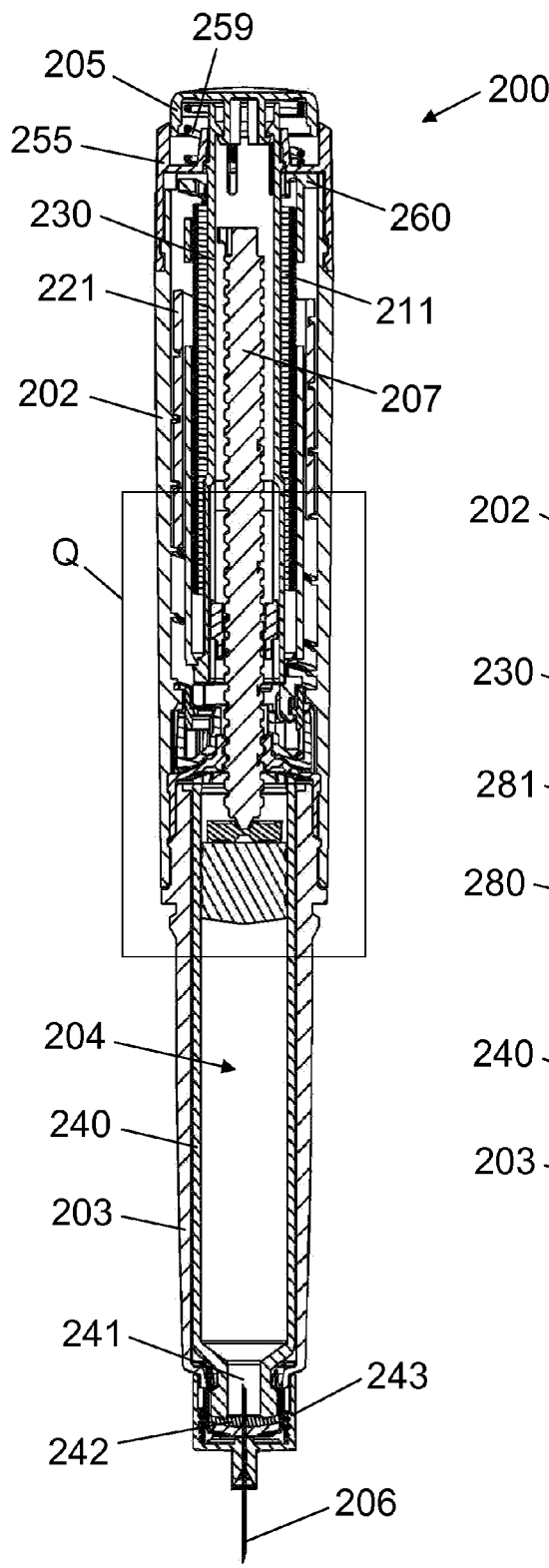
FIG. 20a is a cross sectional view of an injection device according to another embodiment of the invention.
Figure 20B:
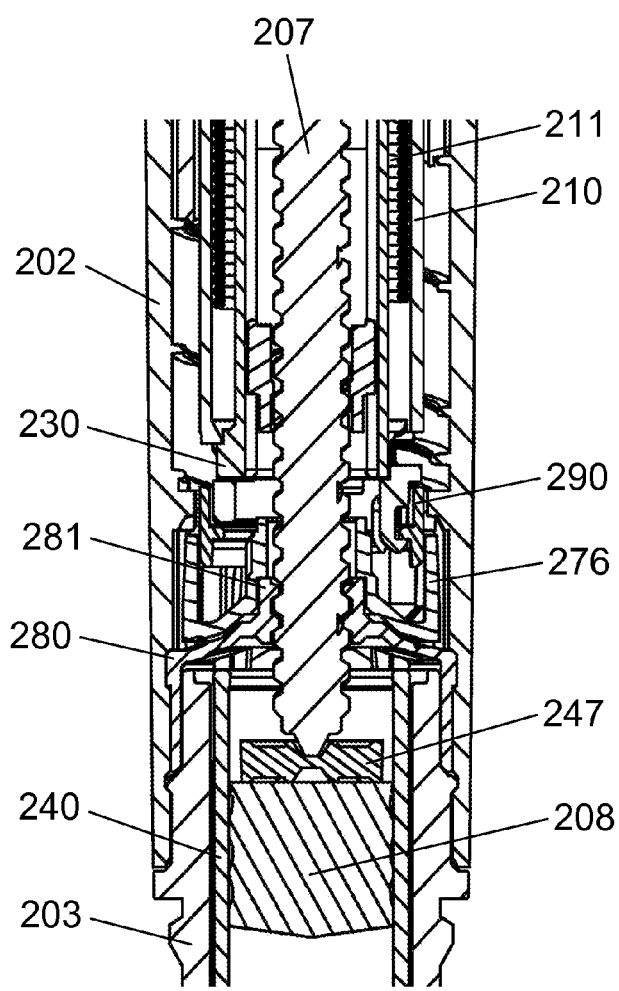
FIG. 20b is a close-up view of a portion of the injection device of FIG. 20a, FIG. 21 is a perspective view of a surpassable one-way mechanism in the injection device of FIG. 20a, FIG. 22 is a cross sectional view of an injection device according to yet another embodiment of the invention.

FIG. 20*a* shows an injection device 200 according to another embodiment of the invention before the delivery of a set dose, and FIG. 20*b* is a close-up view of a portion of the injection device 200 indicated by section Q. The injection device 200 comprises a housing 202 and a cartridge holding part 203 for supporting a cartridge 204 which contains the liquid drug. The liquid drug is positioned between a piston 208, which is capable of moving axially in the cartridge 204, a tubular cartridge wall 240, and a self-sealing septum 242 covering a drug outlet 241. The self-sealing septum 242 is penetrable by an injection needle 206, e.g. in connection with an attachment of a needle assembly to the injection device 200 via a needle hub interface 243. The liquid drug is intended to flow through the injection needle 206 when the piston 208 is advanced in the cartridge 204 by a dedicated piston rod 207 being in contact with the piston 208 via a piston washer 247. A removable cap (not shown) is adapted to be mounted on the injection device 200 to protect the cartridge 204 and to cover the drug outlet 241 when the injection device 200 is not in use.

An injection button 205, being capable of reciprocating axial motion with respect to the housing 202, is shown in a position where it protrudes from the distal end of the housing 202. The injection button 205 is biased in the proximal direction by a button spring 259. A tube 230 is arranged in the housing 202 and translationally locked to the injection button 205, i.e. all axial movements of the injection button 205 are transferred to the tube 230. The tube 230 is translationally and rotationally locked to a driver 210, which is coupled to one end of a torque spring 211. The tube 230 is further rotationally locked to a dose dial button 255. The other end of the torque spring 211 is coupled with a spring base 260 which is fixedly arranged in the housing 202. Thereby, an arrangement is provided which is capable of transferring a rotation of the dose dial button 255 relative to the housing 202 to a rotation of the driver 210 and torsion of the spring 211. Further, a scale drum 221 is arranged in the housing 202 for indicating the size of the dose set by the rotation of the dose dial button 255. The scale drum 221 is rotationally locked to the driver 210 and coupled to the housing 202 via a screw thread. In the zero dose position the scale drum 221 interfaces with the spring base 260, defining a rotational stop for the scale drum 221.

The driver 210 is coupled to a drive clutch 290 via a ratchet mechanism which allows rotation of the driver 210 relative to the drive clutch 290 in one direction but prevents rotation of the driver 210 relative to the drive clutch 290 in the opposite direction. The driver 210 and the drive clutch 290 are further translationally locked which means that all axial movements of the driver 210 are transferred to the drive clutch 290.

The drive clutch 290 is adapted to move axially between a proximal position in which it is rotationally locked to the housing 202 and a distal position in which it is free to rotate with respect to the housing 202. Due to the translational relationship between the injection button 205, the tube 230, the driver 210, and the drive clutch 290 when the injection button 205 is depressed the drive clutch 290 is moved to the distal position and when the injection button 205 is returned by the button spring 259 the drive clutch is moved to the proximal position. The interface between the scale drum 221 and the spring base 260 together with the interface between the scale drum 221 and the driver 210, the ratchet mechanism coupling the driver 210 and the drive clutch 290, and the rotational lock of the drive clutch 290 in the proximal position enable a rotational pre-stressing of the torque spring 211 during assembly of the injection device 200.

When in the distal position the drive clutch 290 engages rotationally with a transfer clutch 276 which is rotationally locked with respect to the piston rod 207. The piston rod 207 is further engaged by a threaded section 281 of a nut 280, which nut 280 is fixedly arranged in the housing 202. Hence, a rotation of the drive clutch 290 will lead to a rotation of the transfer clutch 276 and through that to a rotation of the piston rod 207. The threaded section 281 converts the rotation of the piston rod 207 to a helical motion, whereby the piston rod 207 is displaced axially with respect to the drug outlet 241.

To deliver a dose of the liquid drug the dose dial button 255 is initially turned clockwise (seen from the proximal end of the injection device 200) a number of degrees until the scale drum 221 shows the desired dose through a window (not visible) in the housing 202. This will result in a similar clockwise rotation of the tube 230 and, through the above described rotational relationship, also of the driver 210. When the injection button 205 is not depressed the drive clutch 290 is in its proximal position, i.e. in a position in which it is prevented from rotating with respect to the housing 202. The driver 210 therefore rotates clockwise with respect to the drive clutch 290. This rotation of the driver 210 will twist the torque spring 211 between the driver 210 and the stationary spring base 260. Due to the ratchet interface between the driver 210 and the drive clutch 290 the torque spring 211 will not be able to return to its original state during the dose dialling, so the driver 210 will remain rotationally biased until the injection button 205 is depressed.

When the injection button 205 is depressed against the bias of the button spring 259 the drive clutch 290 will, as described above, move to the distal position. During this shift the drive clutch 290 engages with the transfer clutch 276 and further moves out of engagement with the housing 202, thereby releasing the torque spring 211. The torque from the torque spring 211 then causes the driver 210, the drive clutch 290, and the transfer clutch 276 to rotate counter-clockwise, whereby the piston rod 207 rotates counter-clockwise and, due to the threaded interface with the nut 280, advances the piston 208 in the cartridge 204. Further, the release of the torque spring 211 returns the scale drum 221 to the zero dose position along the screw thread in the housing 202. Since the scale drum 221 and the driver 210 are rotationally interlocked the zero dose position defines the maximum extent of counter-clockwise rotation of the driver 210.

The threaded interface between the nut 280 and the piston rod 207 is non-locking, i.e. an axial force acting on the piston rod 207 in the proximal direction will in principle force the piston rod 207 to rotate clockwise in the threaded section 281 and thereby to move away from the drug outlet 241. However, a coupling between the housing 202 and the transfer clutch 276 resists a clockwise rotation of the piston rod 207 as will be explained in greater detail below.

Figure 21:
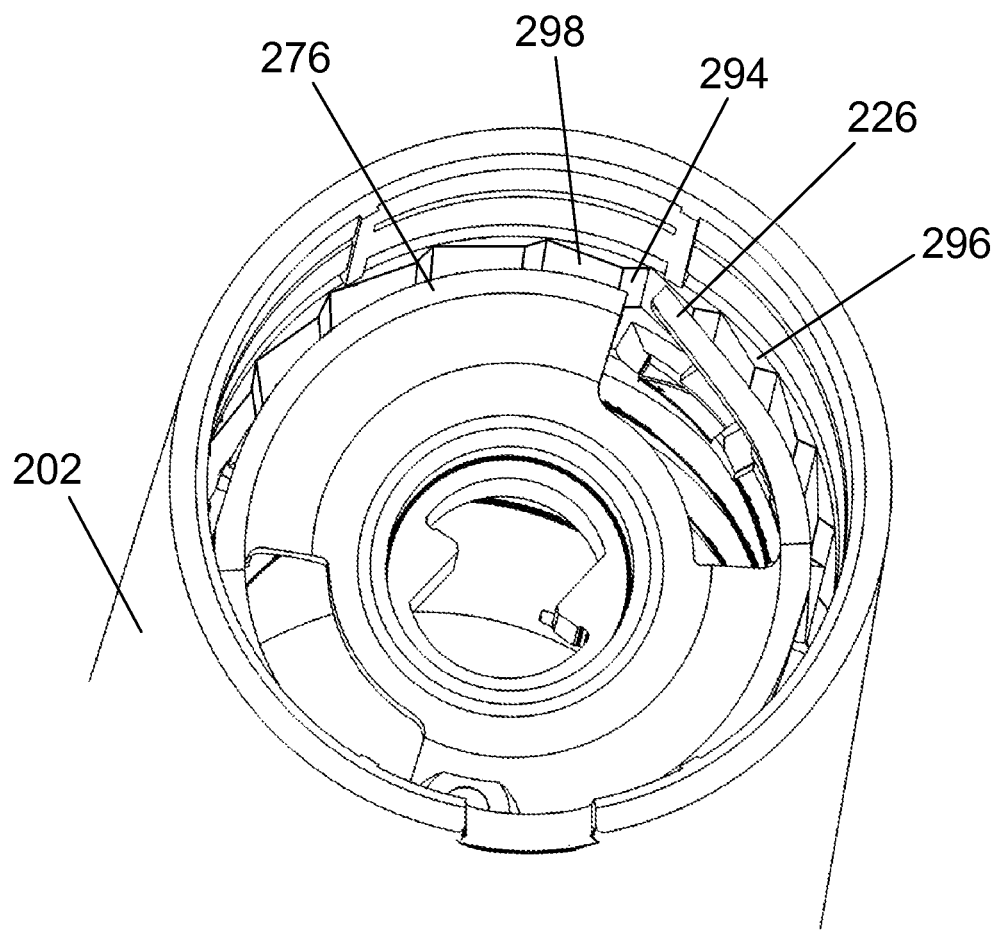

FIG. 21 shows a perspective distal view of the coupling between the housing 202 and the transfer clutch 276. The inner wall of the housing 202 is provided with a circumferential band of teeth 296, and the transfer clutch 276 has a resilient structure in the form of a deflectable arm 226. During drug delivery the transfer clutch 276 rotates counter-clockwise relative to the housing (clockwise in FIG. 21, being a distal view), whereby the arm 226 simply rides over the teeth 296 along respective trailing flanks 298.

When the piston rod 207 is biased clockwise, e.g. caused by a proximally directed force being applied to it, the transfer clutch 276 is also biased clockwise due to the rotational relationship between the two. In FIG. 21, this corresponds to a situation where the transfer clutch 276 tries to rotate counter-clockwise relative to the housing 202. Such relative rotation is resisted by an interaction between the arm 226 and a leading flank 294 of one of the teeth 296. As long as the rotational load on the transfer clutch 276 is smaller than a threshold value this interaction will prevent relative rotation between the transfer clutch 276 and the housing 202.

When the rotational load on the transfer clutch 276 reaches the threshold value, e.g. due to a proximally directed force being applied to the piston rod 207 via the piston 208 because the drug freezes in the cartridge 204, the arm 226 will deflect inwards and ride along the leading flank 294 and further past the tooth edge and down along the trailing flank 298, whereby the transfer clutch 276 is rotationally disengaged from the housing 202 and the piston rod 207 is able to move proximally with respect to the housing 202. The angle between the respective leading flanks 294 and the inner wall of the housing 202 determines the threshold value of the rotational load at which the arm 226 rides over the teeth 296 in the counter-clockwise direction (referring to FIG. 21).

In such a situation, if the drive clutch 290 is in the proximal position (corresponding to the injection button 205 not being depressed in the housing 202) the transfer clutch 276 will rotate with respect to the housing 202 as described in the above and the piston rod 207 will move proximally in the injection device 200 together with the piston 208. When the proximally directed force on the piston rod 207 is discontinued, due to the drug thawing and thereby contracting, the transfer clutch 276 and the piston rod 207 will stay in their respective positions while the piston 208 will be pulled distally, approximately back to its original position in the cartridge 204. This will introduce a slack between the piston 208 and the piston washer 247 which the user must eliminate manually by carrying out a priming operation.

If the drive clutch 290 is in the distal position, however, the clockwise rotation (seen from the proximal end) of the transfer clutch 276 will take place against the bias of the torque spring 211, whereby the torque spring 211 will be stressed beyond its original pre-stressed state. As long as the force is maintained the torque spring 211 will stay thus stressed, but when the force is discontinued the torque spring 211 will return the transfer clutch 276, and thereby the piston rod 207, to their original respective rotational and axial positions in the injection device 200. Hence, the piston rod 207 stays in contact with the piston 208 via the piston washer 247 and the dose accuracy of the injection device 200 is secured automatically. The injection device 200 can be stored with the drive clutch 290 in the distal position due to a user releasable button retaining mechanism (not shown) retaining the injection button 205 in the depressed position against the bias of the button spring 259.

Figures 22, 23:
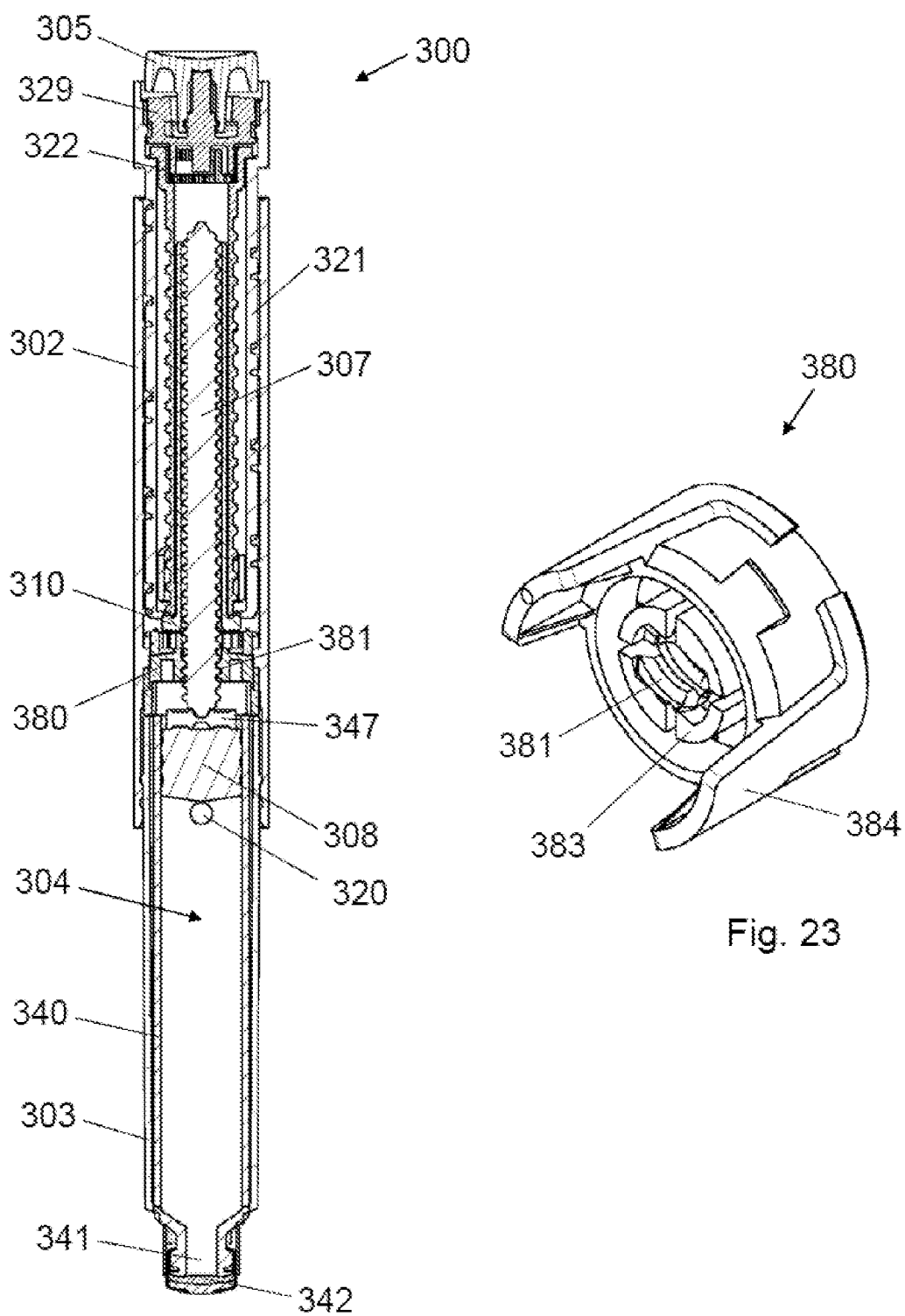
FIG. 23 is a perspective view of a surpassable one-way component in the injection device of FIG. 22.

FIG. 22 shows an injection device 300 according to yet another embodiment of the invention. The injection device 300 comprises a housing 302 and a cartridge holding part 303 for supporting a cartridge 304 which contains the liquid drug and an optional device 320. The liquid drug is positioned between a piston 308, which is capable of moving axially in the cartridge 304, a tubular cartridge wall 340, and a self-sealing septum 342 covering a drug outlet 341. The self-sealing septum 342 is penetrable by an injection needle (not shown), e.g. in connection with an attachment of a needle assembly to the injection device 300. The liquid drug is intended to flow through the injection needle when the piston 308 is advanced in the cartridge 304 by a dedicated piston rod 307 being in contact with the piston 308 via a piston washer 347. A removable cap (not shown) is adapted to be mounted on the injection device 300 to protect the cartridge 304 and to cover the drug outlet 341 when the injection device 300 is not in use. In contrast to the above described injection devices the injection device 300 is not an automatic device, i.e. the force required to advance the piston 308 in the cartridge 304 must be provided by the user.

A helical rib is provided on the inner wall of the housing 202 defining an inner thread with a high pitch. A scale drum 321 is in its outer wall provided with a helical groove defining a corresponding external thread mating said inner thread. The pitch angle of the threads exceeds the angle of friction for the materials forming the parts of the thread connection and consequently the connection is of the non-locking type which induces a relative rotation of the involved parts when the parts are moved axially relative to each other.

Dose indicating numbers are printed on the outer wall of the scale drum 321 so that the number corresponding to a set dose is displayed in a window (not shown) in the wall of the housing 302.

A connector pipe 322 is arranged concentrically with the scale drum 321 and is adapted to move axially a small distance with respect to the scale drum 321 between a proximal position in which the connector pipe 322 and the scale drum 321 are uncoupled and a distal position in which the connector pipe 322 and the scale drum 321 are rotationally interlocked. This axial movement of the connector pipe 322 relative to the scale drum 321 is effectuated by an injection button 305 via a clutch 329 during operation of the injection button 305 in connection with a dose delivery. Further, a driver 310 is arranged concentrically with the connector pipe 322. The driver 310 is splined to the connector pipe 322, whereby these components are rotationally interlocked. The driver 310 is also rotationally interlocked with the piston rod 307, which has a non-circular cross section.

The piston rod 307 is threadedly engaged with a threaded section 381 of a nut 380, which nut 380 is fixedly arranged in the housing 302. This threaded connection is self-locking which implies that a linear force on the piston rod 307 will not result in the piston rod 307 rotating relative to the nut 380.

During dose setting the scale drum 321 is rotated clockwise (seen from the proximal end) until the desired dose is shown in the window. Due to the threaded engagement with the housing 302 the scale drum 321 is thereby screwed proximally out of the housing 302. Because the scale drum 321 and the connector pipe 322 are rotationally decoupled at this point neither the connector pipe 322, nor the driver 310 are rotated by this action.

To expel the set dose the injection button 305 is pushed downwards towards the housing 302. This results firstly in the clutch 329 forcing the connector pipe 322 into connection with the scale drum 321, whereby the connector pipe 322 and the scale drum 321 become rotationally coupled. A continued pressure on the injection button 305 forces the scale drum 321 to rotate counter-clockwise and move axially with respect to the housing 302, along the threaded connection, back to the zero dose position. The counter-clockwise rotation of the scale drum 321 during its return to the zero dose position is transferred to a counter-clockwise rotation of the connector pipe 322, the driver 310, and the piston rod 307, and the piston rod 307 is thereby advanced in the cartridge 304 due to the threaded engagement with the nut 380 converting the rotational input to a helical output. The entire set dose is thus expelled through the drug outlet 341 and the injection needle. The injection button 305 and the clutch 329 are rotationally decoupled which means that the injection button 305 does not rotate during delivery of the drug.

FIG. 23 is a perspective view of the nut 380 and shows a nut body 384 and the centrally located threaded section 381. The threaded section 381 is arranged on the medial side of four flexible jaws 383. The flexible jaws 383 are spaced apart and constitute a circumferentially fragmented tubular portion. If a proximally directed force is applied to the piston rod 307 the self-locking thread connection between the nut 380 and the piston rod 307 will prevent any proximal movement of the piston rod 307 relative to the housing 302 as long as the force is below a threshold value. However, if the force reaches the threshold value because the drug freezes in the cartridge 304 the flexible jaws 383 will deflect radially, whereby the threaded section 381 will disengage from the piston rod 307 and leave the piston rod 307 free to move proximally with respect to the nut 380 together with the piston 308.

When the force is discontinued, because the drug thaws again, the flexible jaws 383 will return to their respective original positions and thereby once again engage with the piston rod 307. The piston 308 will be pulled distally, approximately back to its original position in the cartridge 304, thereby leaving a gap between the piston washer 347 and the piston 308, which the user must eliminate manually by carrying out a priming operation.

Hence, by an injection device according to the present invention a contained drug can freeze and expand in the reservoir without causing damage to vital parts of the injection mechanism. Further, when the drug thaws again the injection mechanism is capable of retrieving its pre-frozen state, either automatically or by the carrying out of a simple, manual priming operation. The dose accuracy of such an injection device is therefore not compromised because the drug temporarily freezes.

The invention claimed is:

1. A medical injection device comprising:
a housing;
a variable volume reservoir containing a liquid drug and comprising an outlet and a movable wall;
an injection mechanism operable to inject a dose of the liquid drug and comprising an actuation member adapted to displace the movable wall in a first direction; and
a coupling mechanism, wherein the injection device is configured to prevent a movement of the actuation member in a second direction substantially opposite the first direction in response to a subjection of the actuation member to a first force being of a magnitude which is smaller than a threshold value and to allow a reversible movement of the actuation member in the second direction in response to a subjection of the actuation member to a second force from the reservoir acting on the actuation member via the movable wall, the second force being of a magnitude which is equal to or greater than the threshold value.

2. An injection device according to claim 1, wherein the injection mechanism further comprises a drive arrangement adapted to cause a movement of the actuation member in the first direction.

3. An injection device according to claim 2, wherein the drive arrangement comprises bias structure for causing the actuation member to be biased in the first direction, and wherein the injection mechanism is configured to allow the actuation member to move a distance in the second direction in response to the second force and to move the actuation member in the first direction substantially the same distance upon a discontinuation of the second force.

4. An injection device according to claim 3, wherein the bias structure comprises a spring member adapted to store and release energy for translational and/or rotational motion.

5. An injection device according to claim 3, wherein the threshold value is substantially equal to the biasing force of the bias structure.

6. An injection device according to claim 2, wherein the coupling mechanism comprises an engagement structure adapted to engage with the drive arrangement when the actuation member is subjected to the first force and further to reversibly disengage with the drive arrangement when the actuation member is subjected to the second force.

7. An injection device according to claim 2, wherein the coupling mechanism comprises an engagement structure providing a coupling between the housing and the actuation member for preventing movements of the actuation member in the second direction relative to the housing, the coupling being configured to reversibly decouple the housing and the actuation member in response to the second force.

8. An injection device according to claim 1, wherein the coupling mechanism comprises an engagement structure adapted to engage with the actuation member when the actuation member is subjected to the first force and further to reversibly disengage with the actuation member when the actuation member is subjected to the second force.

9. An injection device according to claim 1, wherein the actuation member comprises a longitudinal body and a contact surface for engagement with an engagement structure, the contact surface projecting laterally from the body surface.

10. An injection device according to claim 9, wherein the contact surface is at an obtuse angle to the body surface.

11. An injection device according to claim 10, wherein an angle between the contact surface and the body surface lies between 110 and 130 degrees.

12. An injection device according to claim 1, wherein the threshold value lies between 5N and 200N.

13. An injection device according to claim 12, wherein the threshold value lies between 15N and 25N.

14. An injection device according to claim 1, wherein the allowed reversible movement of the actuation member in the second direction is non-destructive.

* * * * *